US010646691B2

(12) United States Patent
Cima et al.

(10) Patent No.: US 10,646,691 B2
(45) Date of Patent: May 12, 2020

(54) INTRAVESICAL DRUG DELIVERY METHODS AND DEVICES

(71) Applicant: Massachusetts Institute of Technology, Cambridge, MA (US)

(72) Inventors: Michael J. Cima, Winchester, MA (US); Heejin Lee, Bedford, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/412,240

(22) Filed: Jan. 23, 2017

(65) Prior Publication Data

US 2017/0157360 A1 Jun. 8, 2017

Related U.S. Application Data

(62) Division of application No. 12/333,182, filed on Dec. 11, 2008, now Pat. No. 9,586,035.

(Continued)

(51) Int. Cl.
*A61M 25/00* (2006.01)
*A61M 25/01* (2006.01)
(Continued)

(52) U.S. Cl.
CPC ....... *A61M 25/0102* (2013.01); *A61K 9/0024* (2013.01); *A61K 9/0034* (2013.01);
(Continued)

(58) Field of Classification Search
CPC .......... A61F 2250/0068; A61K 9/0034; A61M 2205/0216; A61M 2210/1085; A61M 31/002
See application file for complete search history.

(56) References Cited

U.S. PATENT DOCUMENTS 3,077,879 A * 2/1963 Knoch ............... A61F 6/142
128/839
3,089,815 A 5/1963 Kupelwieser
(Continued)

FOREIGN PATENT DOCUMENTS

DE 3332156 A1 3/1985
EP 0572932 A1 12/1993
(Continued)

OTHER PUBLICATIONS

Smith, Julius, Young's Modulus as a Spring Constant, Nov. 22, 2004, <<https://ccrma.stanford.edu/~jos/pasp/Young_s_Modulus_Spring_Constant.html>>, Accessed Jul. 6, 2018.*
(Continued)

*Primary Examiner* — William R Carpenter
(74) *Attorney, Agent, or Firm* — Eversheds Sutherland (US) LLP

(57) ABSTRACT

An implantable medical device is provided for controlled drug delivery within the bladder, or other body vesicle. The device may include at least one drug reservoir component comprising a drug; and a vesicle retention frame which comprises an elastic wire having a first end, an opposing second end, and an intermediate region therebetween, wherein the drug reservoir component is attached to the intermediate region of the vesicle retention frame. The retention frame prevents accidental voiding of the device from the bladder, and it preferably has a spring constant selected for the device to effectively stay in the bladder during urination while minimizing the irritation of the bladder.

26 Claims, 20 Drawing Sheets

Related U.S. Application Data

(60) Provisional application No. 61/084,927, filed on Jul. 30, 2008, provisional application No. 61/007,177, filed on Dec. 11, 2007.

(51) Int. Cl.
   *A61K 9/00* (2006.01)
   *A61K 31/167* (2006.01)
   *A61M 31/00* (2006.01)

(52) U.S. Cl.
   CPC ....... *A61K 31/167* (2013.01); *A61M 25/0108* (2013.01); *A61M 31/002* (2013.01); *A61F 2250/0068* (2013.01); *A61M 2205/0216* (2013.01); *A61M 2210/1085* (2013.01)

(56) References Cited

U.S. PATENT DOCUMENTS

| | | | |
|---|---|---|---|
| 3,312,214 A | 4/1967 | Burdick | |
| 3,398,737 A | 8/1968 | Sheppard et al. | |
| 3,425,411 A * | 2/1969 | Robinson | A61F 6/144 128/839 |
| 3,457,915 A * | 7/1969 | Eshelman | A61F 6/142 128/839 |
| 3,854,480 A | 12/1974 | Zaffaroni | |
| 3,888,975 A | 6/1975 | Ramwell | |
| 3,901,232 A | 8/1975 | Michaels et al. | |
| 3,935,860 A | 2/1976 | Hoff | |
| 3,957,042 A | 5/1976 | Krzaklewski et al. | |
| 4,016,251 A * | 4/1977 | Higuchi | A61F 6/14 128/832 |
| 4,235,236 A | 11/1980 | Theeuwes | |
| 4,326,552 A | 4/1982 | Guerrero | |
| 4,392,848 A | 7/1983 | Lucas et al. | |
| 4,449,980 A | 5/1984 | Millar et al. | |
| 4,475,916 A | 10/1984 | Himmelstein | |
| 4,578,263 A | 3/1986 | Whitehead | |
| 4,629,449 A | 12/1986 | Wong | |
| 4,655,219 A | 4/1987 | Petruzzi | |
| 4,678,463 A | 7/1987 | Millar | |
| 4,731,054 A | 3/1988 | Billeter | |
| 4,871,542 A | 10/1989 | Vilhardt | |
| 4,968,507 A | 11/1990 | Zentner et al. | |
| 4,973,304 A | 11/1990 | Graham | |
| 5,062,829 A | 11/1991 | Pryor et al. | |
| 5,366,738 A | 11/1994 | Rork et al. | |
| 5,368,588 A | 11/1994 | Bettinger | |
| 5,433,218 A * | 7/1995 | Wildemeersch | A61F 6/142 128/832 |
| 5,441,550 A | 8/1995 | Hassenboehler, Jr. et al. | |
| 5,499,997 A | 3/1996 | Sharpe et al. | |
| 5,516,522 A | 3/1996 | Peyman et al. | |
| 5,551,954 A | 9/1996 | Buscemi et al. | |
| 5,709,874 A | 1/1998 | Hanson et al. | |
| 5,788,980 A | 8/1998 | Nabahi | |
| 5,795,591 A | 8/1998 | Lee et al. | |
| 5,797,898 A | 8/1998 | Santini, Jr. et al. | |
| 5,830,230 A | 11/1998 | Berryman et al. | |
| 5,851,217 A | 12/1998 | Wolff et al. | |
| 5,855,906 A | 1/1999 | McClay | |
| 5,869,081 A | 2/1999 | Jackanicz et al. | |
| 5,972,372 A | 10/1999 | Saleh et al. | |
| 5,989,581 A | 11/1999 | Groenewegen | |
| 6,039,967 A | 3/2000 | Ottoboni et al. | |
| 6,039,968 A | 3/2000 | Nabahi | |
| 6,071,305 A | 6/2000 | Brown et al. | |
| 6,083,933 A | 7/2000 | Hahn | |
| 6,086,909 A | 7/2000 | Harrison et al. | |
| 6,139,535 A * | 10/2000 | Greelis | A61M 25/00 604/158 |
| 6,171,298 B1 * | 1/2001 | Matsuura | A61L 17/145 604/891.1 |
| 6,183,461 B1 | 2/2001 | Matsuura et al. | |
| 6,207,180 B1 * | 3/2001 | Ottoboni | A61K 9/0034 424/426 |
| 6,293,923 B1 | 9/2001 | Yachia et al. | |
| 6,398,718 B1 | 6/2002 | Yachia et al. | |
| 6,416,780 B1 | 7/2002 | Passmore et al. | |
| 6,444,224 B1 | 9/2002 | Rathbone et al. | |
| 6,464,999 B1 | 10/2002 | Huo et al. | |
| 6,482,837 B1 | 11/2002 | Wood | |
| 6,491,666 B1 | 12/2002 | Santini, Jr. et al. | |
| 6,524,608 B2 | 2/2003 | Ottoboni et al. | |
| 6,537,193 B1 | 3/2003 | Lennox | |
| 6,682,473 B1 | 1/2004 | Matsuura et al. | |
| 6,712,784 B2 | 3/2004 | Huang | |
| 6,746,421 B2 | 6/2004 | Yachia et al. | |
| 6,749,617 B1 | 6/2004 | Palasis et al. | |
| 6,753,011 B2 | 6/2004 | Faour | |
| 6,808,522 B2 | 10/2004 | Richards et al. | |
| 6,899,890 B2 | 5/2005 | Kirschner et al. | |
| 6,932,810 B2 | 8/2005 | Ryan | |
| 6,951,654 B2 | 10/2005 | Malcolm et al. | |
| 6,973,718 B2 | 12/2005 | Sheppard, Jr. et al. | |
| 6,976,950 B2 | 12/2005 | Connors et al. | |
| 6,976,951 B2 | 12/2005 | Connors et al. | |
| 6,988,983 B2 | 1/2006 | Connors et al. | |
| 7,005,138 B2 | 2/2006 | Mahashabde et al. | |
| 7,074,178 B2 | 7/2006 | Connors et al. | |
| 7,232,421 B1 | 6/2007 | Gambale et al. | |
| 7,521,064 B2 | 4/2009 | Saxena et al. | |
| 7,647,112 B2 | 1/2010 | Tracey et al. | |
| 2003/0059456 A1 | 3/2003 | Malcolm et al. | |
| 2003/0118649 A1 | 6/2003 | Gao et al. | |
| 2003/0118692 A1 | 6/2003 | Wang et al. | |
| 2003/0139800 A1 | 7/2003 | Campbell | |
| 2004/0022824 A1 * | 2/2004 | Li | A61F 2/07 424/423 |
| 2004/0034332 A1 | 2/2004 | Uhland | |
| 2004/0149294 A1 | 8/2004 | Gianchandani et al. | |
| 2004/0220552 A1 | 11/2004 | Heruth et al. | |
| 2004/0260272 A1 | 12/2004 | Friedman et al. | |
| 2005/0234013 A1 | 10/2005 | Parsons | |
| 2005/0234431 A1 | 10/2005 | Williams et al. | |
| 2005/0238733 A1 | 10/2005 | Henry | |
| 2006/0016451 A1 | 1/2006 | Hallinen et al. | |
| 2006/0105010 A1 * | 5/2006 | Rahe | A61F 2/02 424/422 |
| 2006/0122689 A1 | 6/2006 | Kocur et al. | |
| 2006/0234978 A1 | 10/2006 | Marcum | |
| 2006/0259118 A1 | 11/2006 | Pal et al. | |
| 2007/0172507 A1 | 7/2007 | Zupkas et al. | |
| 2007/0172508 A1 | 7/2007 | Zupkas et al. | |
| 2007/0202151 A1 * | 8/2007 | Lee | A61K 9/0034 424/426 |
| 2007/0254014 A1 | 11/2007 | Ahmed et al. | |
| 2007/0255222 A1 * | 11/2007 | Li | A61J 15/0015 604/174 |
| 2008/0051740 A1 | 2/2008 | Sokal et al. | |
| 2009/0004246 A1 | 1/2009 | Woolfson et al. | |
| 2010/0003297 A1 | 1/2010 | Tobias et al. | |
| 2010/0076261 A1 | 3/2010 | Neeman et al. | |
| 2010/0152704 A1 | 6/2010 | Lee et al. | |

FOREIGN PATENT DOCUMENTS

| | | | |
|---|---|---|---|
| WO | 98/31415 A1 | 7/1998 | |
| WO | 9918884 A1 | 4/1999 | |
| WO | 0040234 A1 | 7/2000 | |
| WO | 01/67991 A1 | 9/2001 | |
| WO | 03009882 A2 | 2/2003 | |
| WO | 04037318 A2 | 5/2004 | |
| WO | 05072751 A1 | 8/2005 | |
| WO | 05115245 A1 | 12/2005 | |
| WO | 06121969 A1 | 11/2006 | |
| WO | 2007021964 A2 | 5/2007 | |
| WO | 07115259 A2 | 10/2007 | |
| WO | WO 2007115259 A2 * | 10/2007 | ........... A61F 9/0017 |
| WO | 2008038281 A2 | 4/2008 | |

(56) References Cited

FOREIGN PATENT DOCUMENTS

| WO | 09029958 A2 | 3/2009 |
|---|---|---|
| WO | 09076547 A3 | 6/2009 |
| WO | 2010019507 A2 | 2/2010 |

OTHER PUBLICATIONS

Wright et al, DUROS Osmotic Pharmaceutical Systems for Parenteral & Site-Directed Therapy, Drug Delivery Technology 3(1) 2003.

Wright & Stevenson, Pumps/Osmotic, Encyclopedia of Controlled Drug Delivery, col. 2, New York; John Wiley (1999) pp. 896-920.

http://www.ic-network.com/handbook/instill.html, "About Bladder Instillations", revised Mar. 16, 2006.

Grayson et al, Molecular Release from a Polymeric Microreservoir Device: Influence of Chemistry, Polymer Swelling, and Loading on Device Performance, J. Biomed Mat Res 69A(3); 502-512 (2004).

Estebe, et al., Alkalinization of Intracuff Lidocaine Improves Endotracheal Tube-Induced Emergence Phenomena, Anesth Analg. 2002, pp. 227-230, vol. 94, International Anesthesia Research Society.

Ali, et al., Lidocaine as Endotracheal Tube Cuff Inflating Agent, JAFMC Bangladesh, Jun. 2009, pp. 25-28, vol. 5, No. 1.

Amark, et al., Follow-up of Long-Time Treatment with Intravesical Oxybutynin for Neurogenic Bladder in Children, Eur Urol. 1998, 148-153, S. Garger AG, Basel.

Au, et al., Methods to Improve Efficacy of Intravesical Mitomycin C: Results of a Randomized Phase III Trial, Journal of National Cancer Institute, Apr. 18, 2001, 597-604, vol. 93-8, Oxford University Press.

Bade, et al., A Placebo-Controlled Study of Intravesical Pentosanpolysulphate for the Treatment of Interstitial Cystitis, British Journal of Urology, 79(2); 168-71 (1997).

Beiko, Urinary Tract Biomaterials, Journal of Urology, vol. 171, 2438-2444, (2004).

Birch, et al., Absorption Characteristics of Lignocaine Following Intravesical Instillation, Scand J. of Urology Nephrol, 1994, 359-364, vol. 28, Scandinavian University Press.

Burmeister, et al., Intravscial Instillation of Trospium Chloride, Oxybutynin and Verapamil for Relaxation of the Bladder Detrusor Muscle. A Placebo Controlled, Randomized Clinical Test, 1998, Abstract.

Carr, et al., Evaluation of a Transoral Delivery System for Topical Anesthesia, The Journal of the American Dental Association, Dec. 2001, 1714-1719, vol. 132, American Dental Association.

Clemens, et al., Interstitial Cystitis and Painful Bladder Syndrome, Urological Diseases in Amercia, 2007, 125-154.

Collins, et al., How Common is Prostatitis? A National Survey of Physician Visits. Journal of Urology, 159(4); 1224-1228 (1998).

Curhan, et al., Epidemiology of Interstitial Cystitis: A Population Based Study, Journal of Urology, 161(2); 549-552 (1999).

Dentipatch (lidocaine) Patch [Noven Pharmaceuticals, Inc.], downloaded from http://dailymed.nlm.nih.gov/dailymed/fdaDrugXsi.cfm?id=1543&type=display on Feb. 22, 2007.

Dollo, et al., Endotracheal Tube Cuffs Filled with Lidocaine as a Drug Delivery System In Vitro and In Vivo Investigations, European Journal of Pharmaceutical Sciences, 2001, pp. 319-323, vol. 13, Elsevier Sciences B.V.

Erickson, et al., Interstitial Cystitis, Int. Urogynecol J., 1998, 174-183, vol. 9, Springer-Verlag London Ltd.

Estebe, et al., Alkanlinization of Intra-Cuff Lidocaine and Use of Gel Lubrication Protect Against Tracheal Tube-Induced Emergence Phenomena, British Journal of Anasthesia, 2004, pp. 361-366, vol. 92, No. 3, The Board of Management and Trustees of the British Journal of Anasthesia.

Estebe, et al., Alkalinization of Intracuff Lidocaine: Efficacy and Safety, Anesth Analg, 2005, pp. 1536-1541, vol. 101, International Anesthesia Research Society.

Fraser, et al., The Future of Bladder Control—Intervesical Drug Delivery, a Pinch of Pepper, and Gene Therapy, Reviews in Urology, 2002, 1-11, vol. 4, No. 1.

Gasion, et al., Improving Efficacy of Intravesical Chemotherapy, European Urology, 2006, 225-234, vol. 50, Elsevier B.V.

Gammaitoni, et al., Safety and Tolerability of the Lidocaine Patch 5%, a Targeted Peripheral Analgesic: A Review of the Literature, The Journal of Clinical Pharmacology, 2003, 111-117, vol. 43, American College of Clinical Pharmacology.

Giannantoni, et al., New Frontiers in Intravesical Therapies and Drug Delivery, European Urology, 2006, 1183-1193, vol. 50 Elsevier B.V.

Grayson et al., Multi-pulse Drug Delivery from a Resorbable Polymeric Microchip Device, Nat. Mater 2(11); 1-6 (2003).

Henry, et al., Alkanlinized Intravesical Lidocaine to Treat Interstitial Cystitis: Absorption Kinetics in Normal and Interstitial Cystitis Bladders, Urology, Jun. 2001, 119, vol. 57 (Supplemental 6A).

Henry, et al., Topical anesthesia of the bladder. Can J Anaesth 1999; 46: A61.

Henry, et al., Absorption of Alkalized Intravesical Lidocaine in Normal and Inflamed Bladders: A simple Method for Improving Bladder Anesthesia, The Journal of Urology, Jun. 2001, 1900-1903, vol. 165, Ameircan Urological Association, Inc., U.S.A.

Highley, et al., Intravesical Drug Delivery Pharmacokinetic and Clinical Considerations, Clinical Pharmacokinet, Jul. 1999, 59-73, vol. 37 (1), Adis International Limited.

Jiranantaret, et al., Analgesic Effect of Intraperitoneal Instillation of Bupivacaine for Postoperative Laparoscopic Choloecystectomy, J. Med Assoc Thai, Sep. 2002, 85 (Suppl 3): S897-S903.

Kim, et al., Antimuscarinic Agents Exhibit Local Inhibitory Effects on Muscarinic Receptors in Bladder-Afferent Pathways, 2005, 238-242, Elsevier Inc.

Larsson, et al., Effect of Intraperitoneal Instillation of 32% Dextran 70 on Postoperative Adhesion Formation After Tubal Surgery, 1985, Acta Obstet Gynecol Scand 64:437-441.

Li, et al, Water Based Silicone Elastomer Controlled Release Tablet Film Coating III—Drug Release Mechanisms, Drug Development and Industrial Pharmacy, 1989, 1943-1968, vol. 15(12), Marcel Dekker, Inc.

Malmström, Intravesical Therapy of Superficial Bladder Cancer, Critical Reviews in Oncology, Hematology, 2003, 109-126, vol. 47, Elsevier Science Ireland Ltd.

Morimoto et al., Management of Patients with Recurrent Nephrosis and Intractable Edema by Intraperitoneal Instillation of Icodextrin Solution, Peritoneal Dialysis International, Sep. 2008, vol. 28, No. 5, 559-561.

Parsons et al., Bladder Surface Glycossaminoglycans: An Epithelial Permability Barrier, Journal of Urology, 143 (1); 139-142 (1990).

Parsons, Successful Downregulation of Bladder Sensory Ner4ves with Combination of Heparin and Alkalinized Lidocaine in Patients with Interstitial Cystitis, Urology, 65: 45-48 (2005).

Russell, et al., High-performance Liquid Chromatographic Determination of 17β-Estradiol-3-Acetate Solubilities and Diffusion Coefficients in Silicone Elastomeric Intravaginal Rings, Journal of Chromotagraphy B, 2000, pp. 157-163, vol. 744, Elsevier Science, B.V.

Saitoh et al., Effects of Intravesical Instillation of Resiniferatoxin on Bladder Function and Nociceptive Behaviour in Freely Moving, Conscious Rats, The Journal of Urology, Jan. 2008, 359-364, vol. 179, American Urological Association, U.S.A.

Santus et al., Osmotic Drug Delivery: A Review of the Patent Literature, Journal of Controlled Release 35; 1-21 (1995).

Sconzo, M.D., et al., In Vitro Diffusion of Lidocaine Across Endotracheal Tube Cuffs, Regional Anesthesia, Jan.-Feb. 1990, pp. 37-40.

Spratt, et al, Clinical Delivery System for Intraperitoneal Hyperthermic Chemotherapy, Cancer Research, Feb. 1980 40:256-260.

Stymne, et al., Plasma Concentrations of Lgnocaine and Prilocaine after a 24-h Application of Analgesic Cream (EMLA®) to Leg Ulcers, British Journal of Dermatology, 2001, 530-534, vol. 145, British Association of Dermatologists.

Theeuwes, Elementary Osmotic Pump. Journal of Pharm Sci 64(12); 1987-91 (1975).

(56) References Cited

OTHER PUBLICATIONS

Theoharides, et al., Painful Bladder Syndrome/Interstitial Cystitis: Current Concepts and Role of Nutraceuticals, Seminars in Preventive and Alternative Medicine, 2006, 6-14, vol. 2; Elsevier Inc.

Thombre, et al., Mechanism of Water Transport in Controlled Porosity Osmotic Devices, Journal of Membrane Science, 1989, 279-310, vol. 40, Elsevier Science Publishers B.V.

Tyagi, et al., Local Drug Delivery to Bladder Using Technology Innovations, Urological Clinics of North America, 2006, 519-530, vol. 33, Elsevier Inc.

Vassileva, et al., Novel Biocompitible Intraperitoneal Drug Delivery System Increases Tolerability and Therapeutic Efficacy of Paclitaxel in a Human Ovarian Cancer Xenograft Model, Cancer Chemother Pharmacol, 2007, 60:907-914, Springer-Verlag.

Verma, et al., Formulation Aspects in the Development of Osmotically Controlled Oral Drug Delivery Systems, Journal of Controlled Released, 2002, 7-27, vol. 79, Elsevier Science B.V.

Walker, et al., Intravesical Chemotherapy: In Vitro Studies on the Relationship Between Dose and Cytotoxicity, Urological Research, 1986, 137-140, vol. 14, Springer-Verlag.

Walter, et al., Bioavailability of Trospium Chloride After Intravesical Instillation in Patients with Neurogenic Lower Urinary Tract Dysfunction: A Pilot Study, Neurourology and Urodynamics, 1999, 18:447-453, Wiley-Liss, Inc.

Welk et al., Dyspareunia Response in Patients with Interstitial Cystitis Treated with Intravesical Lidocaine, Bicarbonate, and Heparin, J. Urology, Sep. 2007, 67-70, vol. 71, Elsevier Inc.

Woolfson, et al., Designs of Silicone Reservoir Intravaginal Ring for the Delivery of Oxybutynin, Journal of Controlled Release, 2003, pp. 465-476, vol. 91, Elsevier B.V.

Woolfson, et al., Design of an Intravaginal Ring for the Controlled Delivery of 17β-Estradiol as its 3-Acetate Ester, Journal of Controlled Release, 1999, pp. 319-328, vol. 61, Elsevier Science B.V.

\* cited by examiner

INTRAVESICAL DRUG DELIVERY METHODS AND DEVICES

CROSS-REFERENCE TO RELATED APPLICATIONS

This application is a divisional of U.S. application Ser. No. 12/333,182, filed Dec. 11, 2008, which claims the benefit of U.S. Provisional Application No. 61/007,177, filed Dec. 11, 2007, and U.S. Provisional Application No. 61/084,927, filed Jul. 30, 2008, each of which is incorporated by reference in its entirety.

BACKGROUND OF THE INVENTION

This invention is generally in the field of implantable drug delivery devices, and more particularly in the field of devices for the controlled release of a drug from a device implantable in the bladder or other body lumen or cavity.

Drug delivery is an important aspect of medical treatment. The efficacy of many drugs is directly related to the way in which they are administered. Various systemic methods of drug delivery include oral, intravenous, intramuscular, and transdermal. These systemic methods may produce undesirable side effects and may result in the metabolization of the drug by physiological processes, ultimately reducing the quantity of drug to reach the desired site. Accordingly, a variety of devices and methods have been developed to deliver drug in a more targeted manner. For example, these devices and methods may deliver the drug locally, which may address many of the problems associated with systemic drug delivery.

In recent years, the development of microdevices for local drug delivery is one area that has proceeded steadily. Activation of drug release can be passively or actively controlled. Examples of controlled drug delivery devices are disclosed in U.S. Pat. Nos. 5,797,898, 6,730,072, 6,808,522, and 6,875,208.

These microdevices can be divided roughly in two categories: resorbable polymer-based devices and nonresorbable devices. Polymer devices have the potential for being biodegradable, therefore avoiding the need for removal after implantation. These devices typically have been designed to provide controlled release of drug in vivo by diffusion of the drug out of the polymer and/or by degradation of the polymer over a predetermined period following administration to the patient.

Interstitial cystitis (IC) and chronic prostatitis/chronic pelvic pain syndrome (CP/CPPS) are chronic painful disorders that affect approximately 67 per 100,000 women (Curhan et al., *J. Urol.* 161(2): 549-52 (1999)) and 7 per 100,000 men (Collins et al., *J. Urol.* 159(4): 1224-28 (1998)) in the United States. Both conditions are characterized by chronic pelvic pain, urinary frequency and urgency, and variable degrees of sexual dysfunction. Pentosan polysulfate sodium (PPS) currently is used to treat this condition. However, conventional methods and devices for delivering the drug have significant shortcomings. For example, oral delivery (ELMIRON™, Ortho-McNeil) suffers from low bioavailability, as low as 3% due to a high first pass effect (Parsons et al., *J. Urol.* 153(1): 139-42 (1990)), and causes some mild side effects, such as headaches. PPS delivered intravesically through cystoscopy (with a catheter through the urethra) can provide improved therapeutic effects while reducing the side effects of the drug (Bade et al., *Br. J. Urol.* 79(2): 168-71 (1997)). However, the instillation procedure is painful and requires repeating the procedure twice per week for three months. The repetitive nature of this procedure also engenders high risks for urinary tract infection and bacteremia. Thus, a pronounced need exists for an intravesical drug delivery device that will substantially reduce the number of cystoscopic procedures necessary to deliver an effective amount of PPS or other drugs needed for local delivery over an extended period.

One treatment for IC/PBS entails delivering a lidocaine solution to the bladder via instillation (R. Henry, et al., "Absorption of alkalized intravesical lidocaine in normal and inflamed bladders: a simple method for improving bladder anesthesia," *J Urol,* 165:1900-03, 2001; C. L. Parsons, "Successful downregulation of bladder sensory nerves with combination of heparin and alkalinized lidocaine in patients with interstitial cystitis," *Urology,* 65:45-48, 2005). The bladder lining has such a strong mucous barrier that normal lidocaine has difficulty crossing through it. However, researchers found that if the anesthetic agent is alkalinized with a precise amount of sodium bicarbonate, it improved the anesthetic agent's ability to pass through the mucous to reach and soothe the irritated nerves and tissues beneath. In a conventional procedure, the instillation delivers a bolus dose of lidocaine (or marcaine), heparin, and sodium bicarbonate to the bladder. Over the relatively short time that the solution is present in the bladder, the bladder tissue absorbs the lidocaine to provide the patient with immediate relief from pain and urgency. The absorbed lidocaine also provides continued relief as the lidocaine degrades from the bladder tissue. However, lidocaine has a relatively short half-life, and therefore a relatively high initial concentration of lidocaine may be needed to provide continued relief and the period of relief limited in duration. To achieve sustained relief, subsequent instillations may be required, such as three times per week for two weeks. The frequency of such instillations may be undesirable, as each instillation entails the inconvenience, discomfort, and risk of infection associated with urinary catheterization. The duration of relief may be increased by increasing the initial concentration of lidocaine absorbed into the bladder, such as by increasing the concentration in the solution. However, undesirable systemic effects may result if the initial concentration of lidocaine is too high.

Other therapies could benefit from improved intravesical drug delivery devices, particularly where local delivery of a drug to the bladder is preferred or necessary—such as when the side effects associated with systemic delivery of the drug are unbearable and/or when bioavailability from oral administration is too low. For instance, oxybutynin is used for the treatment of overactive bladder syndrome. Currently, oxybutynin is delivered orally or transdermally. Unfortunately, however, approximately 61% of patients taking the drug experience side effects and approximately 7 to 11% of the patients actually stop treatment due to the severity of the side effects.

Situs Corporation developed an intravesical drug delivery system (UROS infuser device) for the delivery of pharmaceutical solutions of drugs, such as oxybutynin (for the treatment of overactive bladder) and mitomycin C (for the treatment of bladder cancer). The UROS infuser device and methods of making and implanting the device are described in U.S. Pat. Nos. 6,171,298, 6,183,461, and 6,139,535. The UROS infuser device has an elastomeric outer tubing and contains inextensible wire which connects both inner ends. The device has a linear shape during the cystoscopic insertion into the bladder, changes to a crescent shape following implantation and filling of the device with the pharmaceutical solution, and returns to a linear shape after releasing all of the pharmaceutical solution. Extended release of the pharmaceutical solution is controlled by means of a pressure-responsive valve and/or flow-resistive element inside the tubing. The size of the UROS infuser device depends on the size of each inner component, and a considerable portion of the inner volume is used to contain the mechanical components, not drug solution. With a length of approximately 10 cm and an outer diameter of approximately 0.6 cm, the large size of the UROS infuser device can cause significant discomfort and pain to patients, particularly during urological deployment and retrieval of the device. The UROS infuser device also requires an additional surgical procedure for loading of the pharmaceutical solution into the device following implantation. Accordingly, a need exists for an intravesical drug delivery device that is smaller in size, to avoid unnecessary discomfort and pain in patients. In addition, it would be desirable to provide an intravesical drug delivery device that can minimize the number of surgical procedures required for implantation and delivery of drug over the treatment period.

There is also a need to provide sustained delivery over a period of time, and, to accomplish this in the bladder, the device desirably should be retained in the bladder and not excreted before the drug payload can be at least substantially released, even when the drug payload needs to be delivered over a period of several days or weeks. In general, better devices are needed for controlled delivery of drug to the bladder. Desirably, the implantable device should be easy to deliver into (and if necessary, remove from) the bladder with minimum pain or discomfort to the patient.

SUMMARY OF THE INVENTION

In one aspect, an implantable medical device is provided for controlled drug delivery within the bladder, or other body vesicle. In one embodiment, the device includes at least one drug reservoir component comprising a drug; and a vesicle retention frame which comprises an elastic wire having a first end, an opposing second end, and an intermediate region therebetween, wherein the drug reservoir component is attached to the intermediate region of the vesicle retention frame. The retention frame has been determined to be crucial to prevent accidental voiding of the device from the bladder. It preferably has a spring constant selected for the device to effectively stay in the bladder during urination while minimizing the irritation of the bladder.

In one embodiment, the elastic wire may include or consist of a low modulus elastomer, such as silicone, polyurethane, styrenic thermoplastic elastomer, poly(glycerol-sebacate), or a combination thereof. In another embodiment, the elastic wire may include or consist of a superelastic alloy or other shape memory material. For example, the superelastic alloy may comprise a biocompatible nickel-titanium alloy (e.g., Nitinol) or a titanium-molybdenum alloy (e.g., Flexium). In one embodiment, the elastic wire may have a biocompatible polymeric coating, such as silicone, polyurethane, styrenic thermoplastic elastomer, Silitek, Tecoflex, C-flex, and Percuflex.

In one embodiment, the elastic wire in its uncompressed state may be in a curled form, for example, in the form of two or more loops, spirals, or turns. The first and second ends of the elastic wire may be bounded within said one or more loops. The first and second ends of the elastic wire preferably are soft and blunt. The elastic wire in its uncompressed state may be curled in the form of two or more loops, such that the wire can be uncurled into an approximately linear shape to permit the device to be passed through a lumen of a catheter sized for insertion through the urethra of a patient.

In one embodiment, the drug reservoir component includes at least one elongated elastomeric tube having a first end portion and an opposing second end portion and comprising a drug formulation therein, the tube being operable to dispense the drug in vivo at a controlled rate. In one embodiment, the tube is formed of a water permeable material, such as a silicone. In one embodiment, the tube may be formed of a resorbable material. In a preferred embodiment, the tube is formed of a material which comprises or consists of a biocompatible, low modulus elastomer.

A drug formulation may be positioned as a core within the tube. The drug may be dispensed from the device, i.e., released from the tube in vivo (e.g., within the bladder), at a controlled rate by osmosis and/or by diffusion. In one embodiment, the tube may have no aperture, and the drug may, depending on its molecular size and/or structure, diffuse through the tube. In one embodiment, the tube may include one or more apertures, and the drug may be released at a rate controlled by osmosis. In an embodiment, the drug is dispensed at a rate controlled at least in part by diffusion and/or resorption or dissolution of a matrix material, e.g., wherein the tube comprises a composite, such as a polymer/drug composite. The drug formulation preferably is in a solid or semi-solid form. This may facilitate loading the required dosage in a relatively small volume, to minimize undue irritation and discomfort to the patient during and following implantation of the device.

The device may include at least one magnetic element to facilitate cystoscopic withdrawal of the device from the bladder, e.g., after drug delivery has been completed. In certain embodiments, the magnetic element may be located at the first end, the second end, or both the first and second ends of the vesicle retention frame. A soft polymeric coating may be provided over the magnetic elements.

In an alternative embodiment, the device may be formed of resorbable materials such that retrieval of the device is unnecessary, in that it will degrade completely or at least enough to void the remnants of the device.

The aperture(s) for release of the drug are, in at least a preferred embodiment, within a size range where release is controlled osmotically. In one embodiment, the aperture is circular and has a diameter between about 25 μm and about 500 μm. Drug release may occur too quickly if the aperture is too large, and it was found that hydraulic pressure may deform the drug reservoir tubing and possibly alter the aperture, if the aperture size is too small.

The device may further include a floatation feature by the use of low density materials and/or the inclusion of air or another gas in some part of the device. The floatation feature may minimize the possible irritation of the trigone of the urinary bladder. The device also may include, e.g., embedded, radioopaque materials for possible x-ray monitoring of the device.

The size of the tubing lumen of the drug reservoir component determines the possible drug payload volume. In one embodiment, the hollow tube of the drug reservoir component may have an inner diameter between about 0.3 mm and about 2 mm and an outer diameter between about 0.6 mm and about 3 mm. The length(s) of the tubing between the end seals may vary, as may the number of tubing segments attached to any one retention frame.

In a particular embodiment, the implantable medical device for controlled drug delivery may include at least one drug reservoir component which comprises an elongated, water permeable, elastomeric tube having a first end and an opposing second end, a solid or semi-solid drug formulation core within the tube, wherein the tube has one or more apertures for dispensing the drug at a controlled rate; and a vesicle retention frame which comprises an elastic wire having a first end, an opposing second end, and an intermediate region therebetween, wherein the elastic wire comprises a superelastic alloy or other shape memory material, or a low modulus elastomer, and the elastomeric tube of the drug reservoir component is attached to the vesicle retention frame about the intermediate region. In a preferred embodiment, the elastomeric tube is formed of a silicone.

In another aspect, a method is provided for administration of a drug to a local tissue site within/adjacent a body lumen of patient, for example, into a patient's bladder. In one case, the method may comprise providing a lumen device, such as a urethral catheter or cystoscope, which has a distal end, an opposing proximal end, and an open lumen extending therebetween; inserting the distal end of the urethral catheter into the bladder of a patient in need of treatment, where the proximal end of the urethral catheter remains outside of the patient; deforming (e.g., uncurling) the implantable drug delivery device and passing it into the proximal end of the lumen of the urethral catheter; driving the deformed device through the lumen and out of the lumen, whereupon the device returns to its undeformed shape for retention in the bladder; and removing the urethral catheter from the patient. Thereafter, the drug is released in a controlled manner from the drug reservoir component of the device. In certain embodiments of this method, the patient may be in need of treatment for interstitial cystitis, overactive bladder syndrome, or bladder cancer.

In still another aspect, a method of treatment of the bladder in a patient is provided. In one embodiment, the method comprises implanting wholly within the patient's bladder a drug release device; and controllably releasing a local anesthetic agent from the drug delivery device in a manner providing a sustained, therapeutically effective concentration of the anesthetic agent in the urothelium of the bladder, while avoiding high peak plasma concentrations of the anesthetic agent. The anesthetic agent may be lidocaine. In one embodiment, the concentration of the anesthetic agent in the urothelium is at least 1000 times higher than the plasma concentration. In one embodiment, the therapeutically effective concentration of the anesthetic agent in the urothelium is sustained for between 1 and 30 days.

In yet another aspect, a method is provided for treatment of the bladder in a patient, in which the method includes implanting wholly within the patient's bladder a drug release device; and controllably releasing a drug from the drug delivery device in a manner providing a sustained, therapeutically effective concentration of the drug in the urothelium of the bladder, while avoiding high peak plasma concentrations of the anesthetic agent, wherein the drug has a half-life that is equivalent to or within 25% of that of lidocaine.

BRIEF DESCRIPTION OF THE DRAWINGS

FIGS. 3A-3C illustrate an embodiment of a drug reservoir portion of the drug delivery device, wherein FIG. 3A is a side view, FIG. 3B is a cross-sectional view, and FIG. 3C is a cross-sectional view.

DETAILED DESCRIPTION OF THE INVENTION

Figure 1:
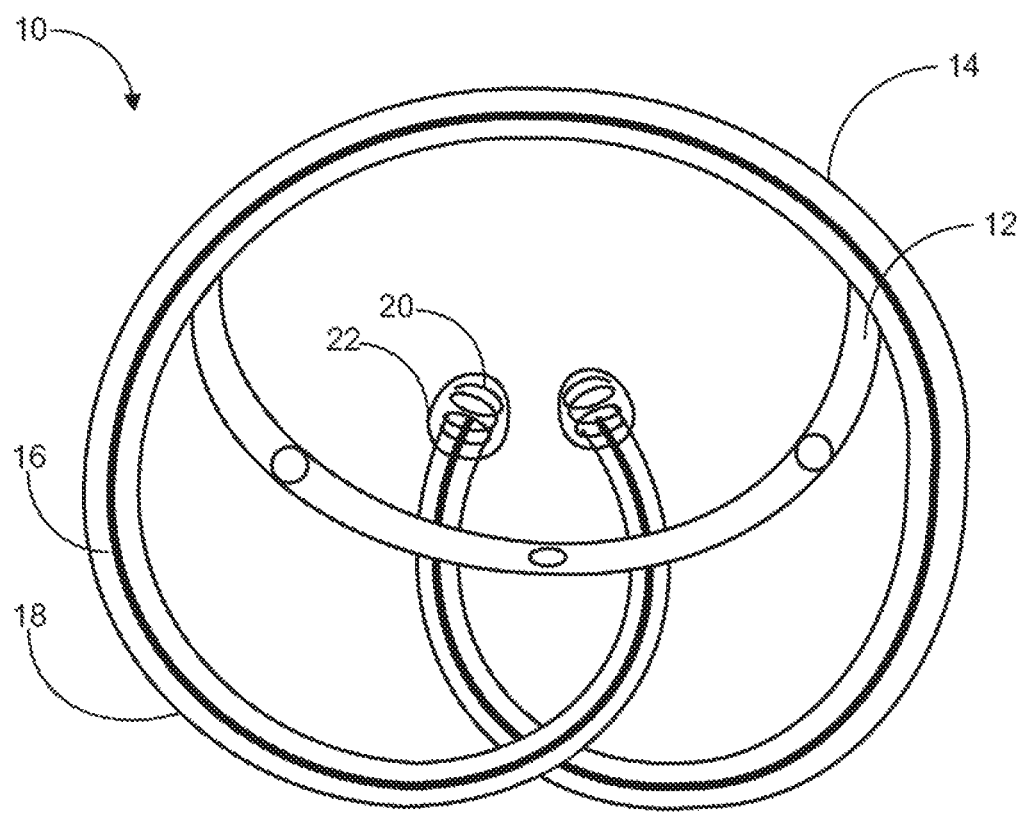
FIG. 1 is a plan view of an embodiment of a drug delivery device in a relatively expanded shape.

Improved drug delivery devices are provided for implantation and retention in the bladder or other body vesicles or lumens. The device can be tailored to release one or more drugs over an extended period of time in a predefined manner, for therapies requiring bolus (one-time), pulsatile, or constant drug delivery.

Importantly, the implantable device is designed for retention within the body, such as within the bladder. That is, the device is designed to resist excretion, such as in response to the forces associated with urination. For example, the device may include a retention frame. The retention frame may be configured into a relatively low profile for deployment into the body, and once implanted may assume a relatively expanded profile to facilitate retention. The device may be highly flexible, so that the drug-loaded device can easily be deformed, such as from a coiled shape to a straightened shape, to permit deployment through a lumen of a catheter into the bladder.

The device may be non-surgically implanted, such as through a cystoscope, and the device may continue delivering a drug long after the cystoscope is removed. In contrast to an indwelling catheter, which may act as a path for bacteria to migrate into the bladder, the implanted device advantageously is able to be located entirely within the bladder. Thus, the opportunity for infection is greatly diminished with the present device.

Regarding the bladder specifically, the device also advantageously addresses many of the deficiencies of conventional treatment options, such as drug delivery via instillation, systemic drug delivery, and drug delivery via devices cystoscopically implanted in the bladder. The present device can be implanted once and can release the drug over an extended period, without requiring surgery or frequent interventions (such as to re-fill the drug reservoir of a conventional device). By limiting the number of procedures required to be performed on the patient during the treatment process, the present local drug delivery system can improve the quality of life of the patient during the treatment process. The drug delivery device can also avoid potential side effects associated with systemic administration of the drug while increasing the amount of drug delivered locally to the bladder.

In one embodiment, the drug delivery device may permit delivering lidocaine (or another cocaine analogue) locally to the bladder over a relatively extended period of time. Thus, the device may provide a beneficial alternative to frequent intravesical instillations of a lidocaine solution for the treatment of IC/PBS. The device may be a passive, non-resorbable device that may be deployed and retrieved by a conventional catheterization, a simple non-surgical outpatient procedure. Unlike intravesical instillation, which loads the bladder with a relatively high concentration of lidocaine over a relatively short time span, the present device may permit continuously releasing a relatively lower level of lidocaine over a relatively longer time span. Thus, the patient may experience sustained relief from the symptoms of IC/PBS without receiving a high initial concentration of lidocaine and without experiencing the discomfort and inconvenience of repeated intravesical installations. Further, it is not necessary to deliver the lidocaine in an alkaline solution in order to achieve effective bladder tissue concentrations.

I. The Implantable Drug Delivery Device

In embodiments, the drug delivery device may include two primary parts or portions: the drug reservoir portion and the vesicle retention frame portion. The drug reservoir portion may be referred to herein as the "device body" and may hold the drug to be delivered into the body. The retention frame portion may be associated with the drug reservoir portion and may facilitate retaining the device in the body. FIG. 1 illustrates an example embodiment of the device 10, the device having both a drug reservoir portion 12 and a retention frame portion 14. In embodiments in which the device is designed for implantation in the bladder, the retention frame portion may impede accidental voiding of the device, and thus the drug reservoir portion, from the bladder.

More specifically, the drug delivery device may be elastically deformable between a relatively expanded shape and a relatively lower profile shape. The relatively lower profile shape may be suited for inserting the drug delivery device into the body. For example, the relatively lower profile shape may be suited for inserting the drug delivery device through a catheter into a cavity of the body, such as through a urethral catheter into the bladder. An example in shown in FIG. 2, which illustrates the device 10 of FIG. 1 in a channel 20, such as a working channel of a cystoscope or other catheter. In such embodiments, the relatively lower profile shape may be a relatively tubular, elongated, or linear shape, such as the shape shown in FIG. 2, so that the device may pass through the catheter. Following passage into the body, the device may assume the relatively expanded shape, such as the shape shown in FIG. 1, which may facilitate retention of the drug delivery device in the body cavity.

In embodiments, the drug delivery device may naturally assume the relatively expanded shape. The device may be elastically deformed into the relatively lower profile shape for insertion into the body, and the device may spontaneously or naturally return to the initial, relatively expanded shape once implanted for retention within the body.

The retention frame may have a certain elastic limit and modulus that allows the device to be introduced into the body in a relatively lower profile shape but then permits the device to return the relatively expanded shape once inside the body. The device may also have a sufficient elastic modulus to impede the device from assuming the relatively lower profile shape once implanted, so as to limit or prevent accidentally expulsion of the device from the body under expected forces. For example, the characteristics of the retention frame may be selected to facilitate retaining the device in the relatively expanded shape despite expected forces in the bladder, such as the hydrodynamic forces associated with urination or contraction of the detrusor muscle. Thus, expulsion from the bladder is impeded or prevented.

In embodiments in which the drug delivery device is designed to be implanted in the bladder, the drug delivery device may be designed to be inserted into and retrieved from the bladder through the urethra cystoscopically. Thus, the device may be sized and shaped to fit through a narrow tubular path of a cystoscope. Typically, a cystoscope for an adult human has an outer diameter of about 5 mm and a working channel having a diameter of about 2.4 mm. Thus, the device may be relatively small in size. For example, when the device is elastically deformed to the relatively lower profile shape, the device may have a total outer diameter that is less than about 2.4 mm, such as between about 2.0 mm and about 2.3 mm.

In addition to permitting insertion, the relatively small size of the device may also reduce patient discomfort and trauma to the bladder. For example, the relatively small size of the device may reduce irritation of the bladder trigone, which is responsible for creating the sensation of urgency of urination. The device may also have a density that is less than the density of urine or water, so that the device may float inside the bladder. Such floatation, although not required, may prevent the device from touching the sensitive trigone region of the bladder near the bladder neck. For example, the device may be formed from relatively low density materials of construction, or air or other gas may be entrapped in the device. The outer surface of the device, furthermore, may be soft and smooth without sharp edges or tips.

The exact configuration and shape of the intravesical drug delivery device may be selected depending upon a variety of factors including the specific site of implantation, route of implantation, drug, dosage regimen, and therapeutic application of the device. Preferably, the design of the device will minimize the patient's pain and discomfort, while delivering a therapeutically effective dose of the drug locally to the patient.

The intravesical drug delivery device can be made to be completely or partially resorbable so that no explantation of the device is required following release of the drug formulation. As used herein, the term "resorbable" means that the device, or part thereof, degrades in vivo by dissolution, enzymatic hydrolysis, erosion, or a combination thereof. This degradation occurs at a time that does not interfere with the intended kinetics of release of the drug from the device. For example, substantial resorption of the device may not occur until after the drug formulation is substantially or completely released. Alternatively, the intravesical drug delivery device may be at least partially non-resorbable, such that the device may be removed following release of the drug formulation. In such embodiments, the device may not be completely resorbable; for example, the device may be partially resorbable so that the device, upon partial resorption, breaks into non-resorbable pieces small enough to be excreted from the bladder. Useful biocompatible resorbable and non-resorbable materials of construction are known in the art. In embodiments, the device may be formed from materials suited for urological applications, such as medical grade silicone, natural latex, PTFE, ePTFE, stainless steel, nitinol, elgiloy (non ferro magnetic metal alloy), polypropylene, polyethylene, polycarbonate, polyester, nylon, or combinations thereof.

The Drug Reservoir Portion

The drug reservoir portion of the device may include an elongated tube. The tube may have a first end and an opposing second end. An interior of the tube may define a reservoir, and a drug formulation core may be housed in the reservoir. The drug formulation may be in a substantially solid form, such as a drug rod, although other configurations are possible. The tube may have one or more apertures for dispensing the drug, such as via osmosis, diffusion, or a combination thereof, among others. In embodiments, the release rate of the drug from the drug reservoir portion may be controlled. For example, a degradable membrane may be disposed over or in one or more of the apertures to control the initiation of release of the drug formulation from the reservoir. As another example, a sheath may be positioned over a portion of the tube to reduce the release rate, such as by reducing the osmotic surface area of the tube or by reducing diffusion through the tube wall. Also, the drug reservoir portion may be formed from a drug polymer composite designed to release at a known rate.

Figure 3A:
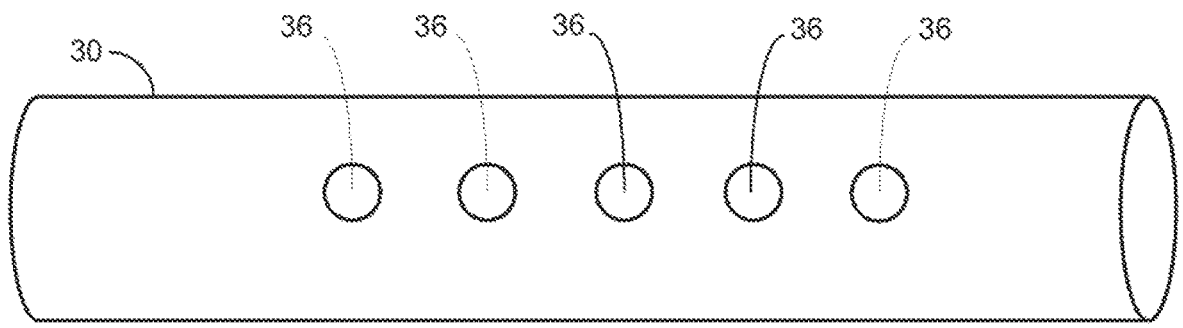
Figure 3B:
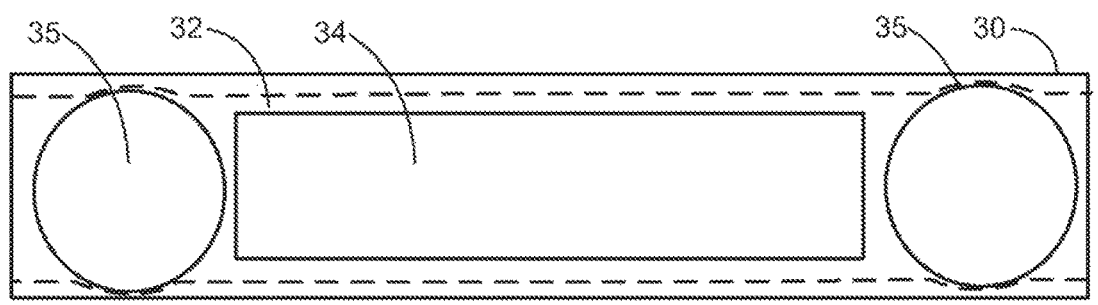
Figure 3C:
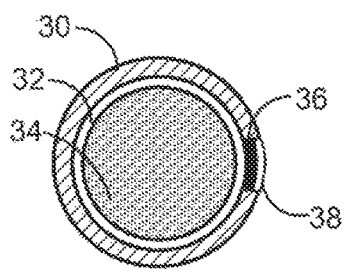

An example of such a drug reservoir portion is shown in FIGS. 3A-3C. As shown, the drug reservoir portion generally includes a body formed from an elastomeric tube 30. The tube 30 defines a reservoir 32 that contains a drug rod 34. Ends of the tube 30 may be sealed with sealing structures 35, further described below. An array of apertures 36 may be disposed in the tube 30 closed off by degradable timing membranes 38.

In a preferred embodiment, the drug reservoir portion operates as an osmotic pump. In such embodiments, the tube may be formed from a water permeable material, such as a silicone. Following implantation, water or urine permeates through the wall of the tube, enters the reservoir, and is imbibed by the drug formulation. Solubilized drug is dispensed at a controlled rate out of the reservoir through the one or more apertures, driven by osmotic pressure in the reservoir. The delivery rate is affected by the surface area of the tube, the thickness of the tube wall, the permeability to liquid of the material used to form the tube, and the shape, size, number and placement of the apertures, among others. The delivery rate can be predicted from the physicochemical parameters defining the particular drug delivery system, according to well known principles, which are described for example in Theeuwes, *J. Pharm. Sci.*, 64(12):1987-91 (1975). Example osmotic pump designs, and equations for such selecting such designs, are described below with reference to Examples 1-3.

In an alternative embodiment, the device may operate essentially by diffusion of the drug from the tube through, for example, one or more of the apertures, the wall of the tube, or a combination thereof. In still other embodiments, the device may operate by a combination of osmosis and diffusion.

In embodiments, the drug reservoir portion may be formed from an elastomeric material, which may permit elastically deforming the device for insertion. For example, the tube may be elastically deformed along with the vesicle retention frame for intravesical implantation, as described in further detail below.

In embodiments, the drug reservoir portion may be made of a biocompatible, water permeable material known in the art, which may permit releasing the drug from the reservoir via osmosis. The drug reservoir portion alternatively may be substantially water impermeable.

In embodiments, the drug reservoir portion may be formed from a material that is both elastomeric and water permeable. An example material is silicone that is both elastomeric and water permeable, although other biocompatible materials may be used.

The length, diameter, and thickness of the tube may be selected based on the volume of drug formulation to be contained, the desired rate of delivery of the drug from the tube, the intended site of implantation of the device within the body, the desired mechanical integrity for the device, the desired release rate or permeability to water and urine, and the desired method or route of insertion into the body, among others. In embodiments, the drug reservoir portion has a length in the range of about 1 cm to about 10 cm, an inner diameter in the range of about 0.3 mm to about 2 mm, and an outer diameter in the range of about 0.6 mm and about 3 mm.

In one embodiment, the device body is non-resorbable. It may be formed of a medical grade silicone tubing, as known in the art. Other examples of suitable non-resorbable materials include synthetic polymers selected from poly(ethers), poly(acrylates), poly(methacrylates), poly(vinyl pyrolidones), poly(vinyl acetates), poly(urethanes), celluloses, cellulose acetates, poly(siloxanes), poly(ethylene), poly(tetrafluoroethylene) and other fluorinated polymers, poly(siloxanes), copolymers thereof, and combinations thereof.

In another embodiment, the device body is resorbable. In one embodiment of a resorbable device, the tube of the body is formed of a biodegradable or bioerodible polymer. Examples of suitable resorbable materials include synthetic polymers selected from poly(amides), poly(esters), poly(ester amides), poly(anhydrides), poly(orthoesters), polyphosphazenes, pseudo poly(amino acids), poly(glycerol-sebacate), copolymers thereof, and mixtures thereof. In a preferred embodiment, the resorbable synthetic polymers are selected from poly(lactic acids), poly(glycolic acids), poly(lactic-co-glycolic acids), poly(caprolactones), and mixtures thereof. Other curable bioresorbable elastomers include poly(caprolactone) (PC) derivatives, amino alcohol-based poly(ester amides) (PEA) and poly (octane-diol citrate) (POC). PC-based polymers may require additional cross-linking agents such as lysine diisocyanate or 2,2-bis (_-caprolacton-4-yl)propane to obtain elastomeric properties.

The drug reservoir portion may be made as described in U.S. Patent Application Publication No. 2007/0202151 to Lee et al., which is incorporated herein by reference.

As mentioned, the tube may be hollow, so that the drug reservoir is defined therein. For example, the tube may be substantially linear, such as substantially cylindrical in shape. Thus, the tube may have a circular cross-section; however, other cross-sectional shapes of the tube are envisioned, such as square, triangle, hexagon, and other polygons, among others. The ends of the tube may be sealed to limit escape of the drug. For example, each end of the tube may be closed off using, a sealing structure, a medical grade silicone adhesive, other sealing means known in the art, or combinations thereof. In embodiments in which the tube is sealed with a sealing structure, the sealing structure may be a ball, a disk, or any other shape suited to plug, close, the end of the tube. An embodiment of a ball-shaped sealing structure 35 in shown in FIG. 3B. Such a sealing structure may be formed from a material a biocompatible metallic material such as stainless steel or a biocompatible polymeric material, such as a biodegradable or bioerodible polymer, although other materials may be used. The sealing structure may have a relatively larger diameter than the inner diameter of the tube, such that the tube stretches to fit snugly about the sealing structure.

In one embodiment, the tube has multiple reservoirs. Multiple apertures may either share a common drug reservoir or have separate reservoirs. Such a multi-reservoir device is useful in at least two particular types of device embodiments: (1) when two or more separate drug formulations are to be delivered from a single device, or (2) when a single drug is to be delivered at two different rates or at different times following implantation, such as when a first dose of the drug is pre-programmed to release at a first time and a second dose is pre-programmed to release at a second, later time. This different pre-programming can be achieved by using different timing membranes for the different reservoirs, for instance with two or more reservoirs, the reservoirs being defined by the inner surface of the tube and at least one partition. The partition structure in the tube may be in the form of a spheroidal object, such as a ceramic bead or other microsphere. The partition structure also may be in the shape of a disk or cylinder. Other configurations are also possible. The partition may be non-resorbable or resorbable. In one embodiment, the partition structure may be made of a biocompatible polymeric material, such as a biodegradable or bioerodible polymer.

Figure 4:
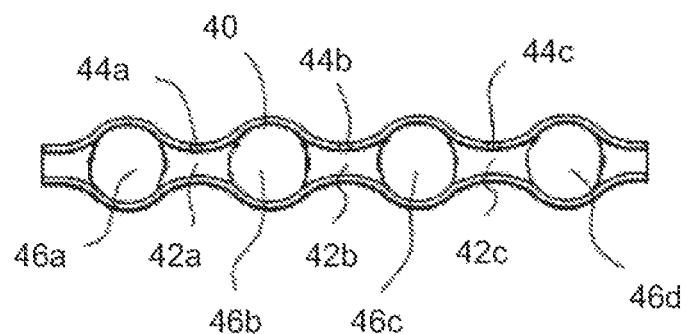
FIG. 4 is a cross-sectional view of an embodiment of a drug reservoir portion that includes multiple reservoirs separated by partition structures.

An embodiment of such a drug reservoir portion is shown in FIG. 4. The drug reservoir portion has a body that includes a linear tube 40. The hollow space in the tube 40 is partitioned into three reservoirs 42a, 42b, 42c, each of which has a single corresponding aperture 44a, 44b, 44c. The reservoirs 42 are defined by the inner surface of the tube 40, meaning the sidewall of the tube, and by spherical partition structures 46a, 46b, 46c and 46d spaced within the interior space of the tube. As can be seen, the partition structures are secured in place within the tube 40 by having a larger diameter than the inner diameter of the unstretched elastomeric tube, which causes the tube to stretch and snugly fit around the partition structures, sealing each reservoir.

In embodiments, partitioned reservoirs may prevent an aperture with a faster biodegradable membrane from monopolizing the release of the loaded drug material, potentially leaving little or no drug material for release from apertures with subsequently degrading membranes. Providing a separate reservoir for each release aperture may increase the effect of multiple biodegradable timing membranes.

In a preferred embodiment, the total volume of the reservoir (or combined reservoirs) is sufficient to contain all the drug needed for local delivery over the course of a single therapy. That is, the drug reservoir portion desirably contains all of the doses of drug anticipated, so that multiple cystoscopic procedures are not needed, or are reduced in number/frequency to complete the therapy prescribed for a given disease or condition.

Apertures

In one embodiment, the device body includes one or more apertures or orifices through the sidewall or end of the tube. The one or more apertures provide a passageway to release the drug formulation from the drug delivery device. In one embodiment, the device includes an array of two or more discrete apertures in spaced positions in the tube. The two or more apertures may be in fluid communication with a single reservoir or with a plurality of reservoirs. The placement of apertures near the portion of the tube which will be folded during cystoscopic insertion may be avoided in order to prevent the possible tear of polymer biodegradable membranes on the apertures. Embodiments of apertures 36 are shown on the tube 30 of the drug reservoir portion shown in FIG. 3A.

The size of the aperture may be selected to provide a controlled rate of release of the drug. In embodiments in which the device is intended to operate primarily as an osmotic pump, the size of the aperture may be selected such that the aperture is small enough to minimize or otherwise reduce diffusion of the drug through the aperture. The apertures may also be configured to prevent excessive buildup of hydrostatic pressure in the tube, which may increase the volume of fluid in the reservoir, resulting in swelling of tube. For example, an increase in hydrostatic pressure within the reservoir may be prevented by the ensuring the size of the aperture is large enough and/or by spacing a number of apertures along the length of the tube. Within these constraints on aperture size and number, one may then vary the size and number of such apertures employed in a single device (or in a single reservoir) in order to provide a needed total rate of drug released. In exemplary embodiments, the diameter of the aperture is between about 20 μm and about 300 μm (e.g., 20 to 100 μm, 25 to 75 μm, etc.). In one example, the aperture is circular and has a diameter between about 25 μm and about 500 μm. In another example, the aperture is circular and has a diameter between about 20 μm and about 75 μm. In one particular example, the aperture has a diameter of about 50 μm. In embodiments where the device operates primarily by diffusion, the apertures may be in this range or larger.

A single device may have apertures of two or more different sizes. The aperture typically is circular in shape, although other shapes are possible and envisioned, and will typically depend on manufacturing considerations.

In one embodiment, the apertures are drilled by laser ablation through the wall of the tube, such as the silicone tube. For example, the aperture may be generated using an ultraviolet excimer laser micromachining system. In such embodiments, the aperture may be slightly tapered from an exterior of the tube to an interior of the tube. For example, the aperture may have a diameter of about 55 μm along the outer surface of the tube wall, and the aperture may have a diameter of about 45 μm along the inner surface of the tube wall, although any other configuration is possible. The apertures may then be covered with biodegradable timing membranes. A person of skill may be able to use laser ablation to drill in a medical grade polymer, via either through-hole drilling or depth-controlled drilling, to create a well-defined hole with a diameter as small as 0.050 mm. Therefore, the apertures may be created before or after the drug is loaded into the tube.

Figure 5:
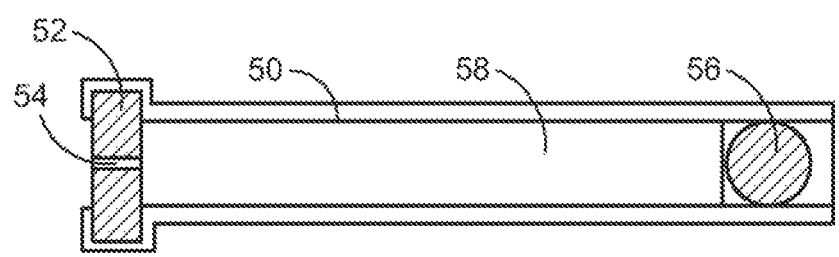
FIG. 5 is a cross-sectional view of an embodiment of a drug reservoir portion having an orifice structure at one end and an aperture formed through the orifice structure.

In another embodiment, one or more apertures may be formed in an orifice structure disposed in an end of the tube. Such an embodiment is shown in FIG. 5. The drug reservoir portion may have a tubular silicone body 50 with a precision orifice structure 52 plugging one end of the central bore of the body. The orifice structure 52 may include an aperture 54. A sealing structure, such as a microbead 56, may plug the opposing end of the tube, and a drug formulation 58 may be disposed in the reservoir defined between the orifice structure 52 and the microbead 56. The orifice structure may be a precision orifice known in the art (available for example from Bird Precision Orifices, Swiss Jewel Company). The orifice can be inserted within and/or attached to the silicone tubing with silicone adhesives. In one example, the device may include silicone tubing having an inner diameter of 305 μm and outer diameter of 635 μm, with a precision orifice structure made of ruby or sapphire and having an outer diameter of about 1.5 mm or smaller.

Degradable Membranes

In one embodiment, each of the one or more apertures has a degradable membrane disposed over or in each of the apertures (e.g., in register with the aperture), to control the time at which release of the drug formulation begins. In one embodiment, the degradable membrane is in the form of a uniform coating covering the outer surface of the tube of the device body. In another embodiment, discrete degradable membranes may be provided substantially within the aperture. Combinations of two or more degradable membranes may be used to control release from one aperture.

The thickness of the degradable membrane in a particular system will depend for example on the chemistry and mechanical properties of the material of construction selected for the degradable membrane (which primarily govern the rate of degradation), as well as on the desired time of delay of drug release for the particular drug delivery device. See, e.g., Richards Grayson, et al., "Molecular release from a polymeric microreservoir device: Influence of chemistry, polymer swelling, and loading on device performance" Wiley InterScience (6 Apr. 2004); Richards Grayson, et al., "Multi-pulse drug delivery form a resorbable polymeric microchip device" Nature Materials, Advance Online Publication (19 Oct. 2003); U.S. Pat. No. 6,808,522. In one embodiment, the degradable membrane has a thickness between about 100 μm and about 200 μm, such as between 145 μm and 160 μm.

The membranes may be formed of a biocompatible material. In one embodiment, the membranes are formed of a resorbable synthetic polymer such as polyester, a poly (anhydride), or a polycaprolactone. In another embodiment, the membranes are formed of a resorbable biological material such as cholesterol, other lipids and fats.

For embodiments of these devices in which it is desired to release drug over a short period of time, the degradable membrane may be fabricated from quickly disintegrating materials including, for example, poly(lactide-co-glycolide) copolymers containing a high glycolide content, copolymers of poly(lactones) with fast degradation times, certain poly (anhydrides), hydrogels, oligosaccharides, and polysaccharides. For applications in which a longer or delayed release time is desirable, the degradable membrane may be fabricated from materials that take longer to disintegrate, for example, resorbable biological materials such as cholesterol, other lipids and fats, and lipid bilayers, polymers such as poly(caprolactone) or certain poly(anhydrides), and PLGA copolymers with high lactic acid content.

In certain embodiments, the degradable membranes permit achieving complex release profiles from a single drug delivery device. In one embodiment, this may be accomplished by having different membranes over different apertures, either to the same reservoir or different reservoirs. In one case, one of the membranes is formed of a first material and another of the membranes is formed of a second material, wherein the first material has a different degradation rate in vivo compared to the second material. In another case, one of the membranes has a first thickness and the other of the membranes has a second, greater thickness. These approaches may be mixed and matched to design a particular release profile, alone or in combination with kinetics altering approaches based on formulating the drug with a release controlling excipient material, or covering a portion of the drug reservoir portion with a release altering sheath, as described below.

The Drug Formulation

The drug formulation can include essentially any therapeutic, prophylactic, or diagnostic agent that would be useful to deliver locally to a body cavity. The drug formulation may consist only of the drug, or may include one or more pharmaceutically acceptable excipients.

In a preferred embodiment, the drug formulation is in a solid or semi-solid form in order to reduce the overall volume of the drug formulation and thereby reduce the size of the device—to promote ease of implantation. The semi-solid form may be, for example, an emulsion or suspension; a gel or a paste. In one example, the drug formulation is in the form of a solid drug rod. Embodiments of drug rods, and methods of making such drug rods, are described in U.S. patent application Ser. No. 11/463,956, which is incorporated by reference in its entirety. The drug rods may be formed by adapting other extrusion or casting techniques known in the art. For example, a drug rod comprising chondroitin 6-sulfate or chondroitin sulfate C may be formed by filling a tube with an aqueous CSC solution and then allowing the solution to evaporate. As another example, a drug rod comprising lidocaine may be formed may be formed by filling a tube with an aqueous solution comprising lidocaine, allowing the solution to evaporate, and then crystallizing the resulting gel. In many embodiments, the drug formulation desirably includes no or a minimum quantity of excipient for the same reasons of volume/size minimization.

In other embodiments, the drug formulation may be in the form of a liquid, solution, suspension, emulsion, emulsions, colloidal suspensions, slurries, gel mixtures such as hydrogels, or combination thereof. The drug formulation may be in a powder or microparticle form, for example, as a hydratable or water soluble solid.

Pharmaceutically acceptable excipients are known in the art and may include viscosity modifiers, bulking agents, surface active agents, dispersants, osmotic agents, diluents, and other non-active ingredients of the formulation intended to facilitate handling, stability, dispersibility, wettability, and/or release kinetics of the drug (i.e., the active pharmaceutical ingredient or diagnostic agent).

In a particular embodiment, the intravesical drug delivery device is used to provide pain relief to the patient. A variety of anesthetic agent, analgesic agents, and combinations thereof may be used. Representative examples of suitable such agents include lidocaine hydrochloride, procaine hydrochloride, salicyl alcohol, tetracaine hydrochloride, phenazopyridine hydrochloride, acetaminophen, acetylsalicylic acid, flufenisal, ibuprofen, indoprofen, indomethacin, naproxen, codeine, oxycodone, and fentanyl citrate. In a preferred embodiment, the device is used to deliver one or more local anesthetic agents. The local anesthetic agent may be a cocaine analogue. In particular embodiments of the device, the local anesthetic agent is an aminoamide, an aminoester, or a mixture thereof. Combinations of different aminoamides or combinations of different aminoesters are envisioned. Representative examples of possible aminoamides include lidocaine, prilocaine, mepivacaine, and ropivacaine. Representative examples of possible aminoesters include benzocaine, procaine, proparacaine, and tetracaine. These local anesthetics typically are weak bases and are usually formulated as a salt, such as the hydrochloride salt, to render them water-soluble.

In a preferred embodiment, the present intravesical drug delivery device is used to treat inflammatory conditions such as interstitial cystitis, radiation cystitis, painful bladder syndrome, prostatitis, and urethritis. Non-limiting examples of specific drugs for these conditions include lidocaine hydrochloride, glycosaminoglycans (e.g., chondroitin sulfate, sulodexide), pentosan polysulfate sodium (PPS), dimethyl sulfoxide (DMSO), oxybutynin, mitomycin C, heparin, flavoxate, or a combination thereof.

The present intravesical drug delivery device can be used to treat urinary incontinence, including urge incontinence and neurogenic incontinence. Drugs that may be used include anticholinergic agents, antispasmodic agents, antimuscarinic agents, β-2 agonists, norepinephrine uptake inhibitors, serotonin uptake inhibitors, calcium channel blockers, potassium channel openers, and muscle relaxants. Representative examples of suitable drugs for the treatment of incontinence include oxybutynin, S-oxybutytin, emepronium, verapamil, imipramine, flavoxate, atropine, propantheline, tolterodine, rociverine, clenbuterol, darifenacin, terodiline, trospium, hyoscyamin, propiverine, desmopressin, vamicamide, YM-46303 (Yamanouchi Co., Japan), lanperisone (Nippon Kayaku Co., Japan), inaperisone, NS-21 (Nippon Shinyaku Orion, Formenti, Japan/Italy), NC-1800 (Nippon Chemiphar Co., Japan), ZD-6169 (Zeneca Co., United Kingdom), and stilonium iodide.

In another embodiment, the present intravesical drug delivery device is used to treat urinary tract cancer, such as bladder cancer and prostate cancer. Drugs that may be used include antiproliferative agents, cytotoxic agents, chemotherapeutic agents, or a combination thereof. Representative examples of suitable drugs for the treatment of urinary tract cancer include Bacillus Calmette Guerin (BCG) vaccine, cisplatin, doxorubicin, methotrexate, vinblastine, thiotepa, mitomycin, fluorouracil, leuprolide, flutamide, diethylstilbestrol, estramustine, megestrol acetate, cyproterone, flutamide, and cyclophosphamide. The drug treatment may be coupled with a conventional radiation or surgical therapy targeted to the cancerous tissue.

In still another embodiment, the present intravesical drug delivery device is used to treat infections involving the bladder, the prostate, and the urethra. Antibiotics, antibacterial, antifungal, antiprotozoal, antiviral and other antiinfective agents can be administered for treatment of such infections. Representative examples of suitable drugs for the treatment of infections include mitomycin, ciprofloxacin, norfloxacin, ofloxacin, methanamine, nitrofurantoin, ampicillin, amoxicillin, nafcillin, trimethoprim, sulfa, trimethoprimsulfamethoxazole, erythromycin, doxycycline, metronidazole, tetracycline, kanamycin, penicillins, cephalosporins, and aminoglycosides.

Other drugs and excipient may be used for other therapies and at other non-bladder body cavity sites. Combinations of two or more drugs, stored in (and released from) the same or separate reservoirs in the device are envisioned.

The excipient of the drug formulation may be a matrix material, selected to modulate or control the rate of release of the drug from the reservoir. In one embodiment, the matrix material may be a resorbable or non-resorbable polymer as described above. In another embodiment, the excipient comprises a hydrophobic or amphiphilic compound, such as a lipid (e.g., selected from fatty acids and derivatives, mono-, di- and triglycerides, phospholipids, sphingolipids, cholesterol and steroid derivatives, oils, vitamins and terpenes), The drug formulation may provide a temporally modulated release profile or a more continuous or consistent release profile. Pulsatile release can be achieved from a plurality of reservoirs. For example, different degradable membrane can be used to by temporally stagger the release from each of several reservoirs.

The Vesicle Retention Frame

As mentioned above, the drug delivery device includes a vesicle retention frame portion. The retention frame portion is associated with the drug reservoir portion and permits retaining the drug reservoir portion in the body, such as in the bladder. The retention frame may be elastically deformed between a relatively expanded shape and a relatively lower profile shape. For example, the retention frame may naturally assume the relatively expanded shape, may be manipulated into the relatively lower profile shape for insertion into the body, and may spontaneously return to the relatively expanded shape upon insertion into the body.

The retention frame in the relatively expanded shape may be shaped for retention in a body cavity, and the retention frame in the relatively lower profile shape may be shaped for insertion into the body through a lumen of a catheter. For example, the retention frame may be elastically deformable between a shape suited for insertion into the body through the working channel of cystoscope, and a shape suited for retention in the bladder even when exposed to the forces associated with urination or contraction of the detrusor muscle. An example of such an embodiment is shown in FIGS. 1-2, wherein the retention frame assumes a pretzel shape when in the expanded position, and the retention frame assumes a relatively elongated, linear shape when in the lower profile position.

To achieve such a result, the retention frame may have an elastic limit, modulus, and/or spring constant selected to impede the device from assuming the relatively lower profile shape once implanted. Such a configuration may limit or prevent accidental expulsion of the device from the body under expected forces. For example, the device may be retained in the bladder during urination or contraction of the detrusor muscle.

In a preferred embodiment, the retention frame includes an elastic wire. In one embodiment, the elastic wire may comprise a superelastic alloy or other shape memory material, known in the art. For example, the superelastic alloy may comprise a biocompatible nickel-titanium alloy (e.g., Nitinol) or a titanium-molybdenum alloy (e.g., Flexium). Biodegradable, biocompatible shape memory polymers are described in U.S. Pat. No. 6,160,084 to Langer et al. In another embodiment, the elastic wire is or includes a relatively low modulus elastomer. Low modulus elastomers may be relatively less likely to cause irritation to the bladder or to cause an ulcer once implanted. Furthermore, some low modulus elastomers may be completely biodegradable, which may permit creating a device that need not be removed following implantation and drug delivery. Examples of low modulus elastomers include polyurethane, silicone, styrenic thermoplastic elastomer, and poly(glycerol-sebacate) (PGS). The elastic wire may be coated with a biocompatible polymer, such as a coating formed from one or more of silicone, polyurethane, styrenic thermoplastic elastomer, Silitek, Tecoflex, C-flex, and Percuflex.

Figure 2:
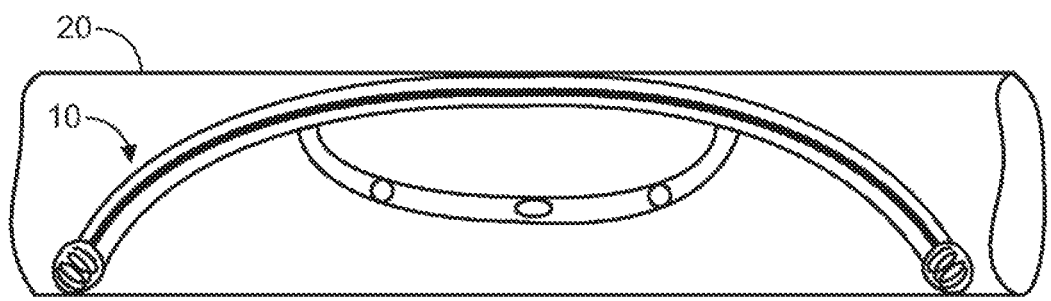
FIG. 2 is a plan view of the embodiment of the drug delivery device shown in FIG. 1, illustrating the drug delivery device in a relatively lower profile shape inside of a catheter.

For example, in the embodiment shown in FIGS. 1-2, the retention frame 14 includes an elastic wire 16 formed from a superelastic alloy and covered in a polymer coating 18. The elastic wire 16 may be, for example, a nitinol wire. The polymer coating 18 may be, for example, a silicone sheath. In the relatively expanded or pretzel shape shown in FIG. 1, the device 10 may occupy an area having dimensions suited to impeded expulsion from the bladder. In the relatively lower profile shape, shown in FIG. 2, the device 10 may occupy an area suited for insertion into the body. Thus, the device 10 may fit in a catheter 20 when in the relatively lower profile shape, such as the working channel of a cystoscope. Due to the properties of the elastic wire, the device may function as a spring. Thus, the device may deform in response to a compressive load but may spontaneously return to its initial shape once the load is removed. The polymer coating may make the outer surface of the device relatively smooth and soft, so that irritation of the bladder is avoided.

In embodiments, the retention frame may also include a radio-opaque material, which may improve the visibility of the device to x-ray or other imaging techniques. In the embodiment shown in FIGS. 1-2, for example, the radio-opaque material is a platinum wire 20 wound about ends of the elastic wire 16, although the platinum wire 20 may be wound about other portions of the elastic wire 16. A smoothening material may also be applied to ends of the elastic wire to reduce the bluntness of the ends. In the embodiment shown in FIGS. 1-2, for example, the smoothening material 22 is an ultraviolet-curable epoxy applied to the ends. The ultra-violet epoxy may also assist with retaining the platinum wire 20 in place.

In embodiments in which the retention frame assumes a pretzel shape, the retention frame may be relatively resistant to compressive forces. A pretzel shape essentially comprises two sub-circles, each sub-circle having its own smaller arch and the sub-circles sharing a common larger arch. When the two sub-circles are first compressed together, the largest arch absorbs the majority of the compressive force and begins deforming. With continued application of the compressive force, the smaller arches of the two sub-circles overlap. Subsequently, all three of the arches resist the compressive force. The resistance to compression of the device as a whole increases once the two sub-circles overlap. Such a configuration may prevent collapse of the device as the bladder contracts during urination, to impede accidental voiding from the bladder. Example 4 explains this result in greater detail.

In embodiments in which the retention frame comprises a shape memory material, the material used to form the frame may "memorize" the relatively expanded shape and may spontaneously assume the relatively expanded shape upon the application of heat to the device. For example, the retention frame may be designed to return to the relatively expanded shape when exposed to body temperatures, so that the device may expand upon entering the bladder.

The retention frame may be in a form having a high enough spring constant to retain the device within a body cavity, such as the bladder. This may be accomplished by forming the retention frame from a high modulus material or a low modulus material. Particularly, in embodiments in which the retention frame is formed from a relatively low modulus material, the retention frame may be formed into a configuration having a diameter and/or a shape that provides an appropriate spring constant. In one case, the elastic wire may comprise a low modulus elastomer in a form having a spring constant without which the elastic wire would otherwise experience significant deformation when subjected to the forces associated with urination. For example, the elastic wire of the retention frame may include one or more windings, coils, spirals, or combinations thereof, which may reduce the tendency of the elastic wire to deform during urination. In other words, the elastic wire may act as a spring due to the windings, coils, and/or spirals, even in cases in which the elastic wire is formed from a low modulus elastomer, such as polyurethane or silicone.

The windings, coils, or spirals may be specifically designed to achieve a desirable spring constant. In various embodiments, the spring constant may be in the range of about 3 N/m to about 60 N/m. For example, the spring constant may be in the range of about 3.6 N/m to about 3.8 N/m. Such a spring constant may be achieved by one or more of the following techniques: increasing the diameter of the elastic wire used to form the frame, increasing the curvature of one or more windings of the elastic wire, and adding additional windings to the elastic wire. Example spring constants for certain low modulus wires are provided in Example 5, below.

Figure 6:
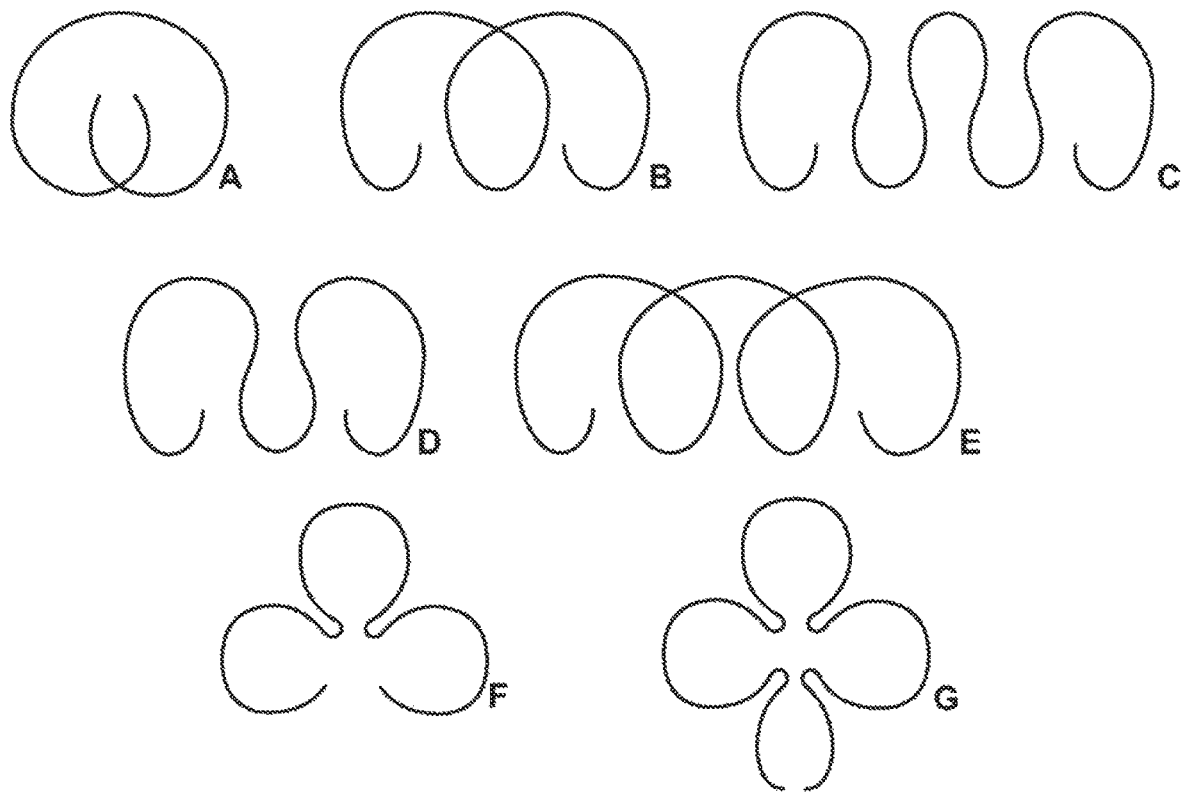
FIG. 6 illustrates example shapes for a vesicle retention frame portion of the drug delivery device, the shapes including one or more loops, curls, or sub-circles.
Figure 7:
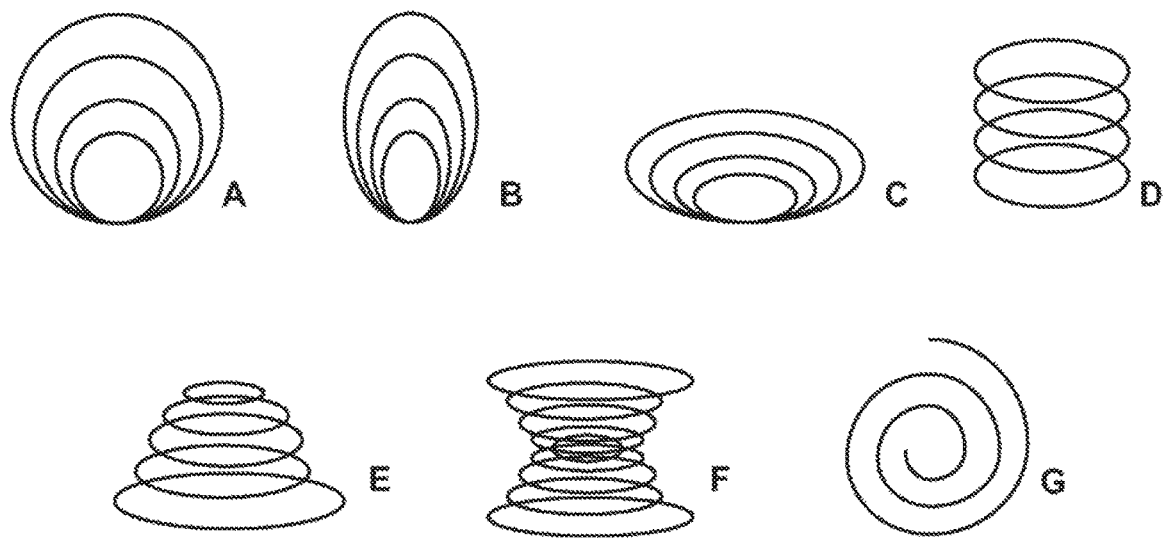
FIG. 7 illustrates example shapes for the frame that include one or more circles or ovals arranged in a two-dimensional or a three-dimensional configuration.

The windings, coils, or spirals of the frame may have a number of configurations. For example, the frame may be in a curled configuration, such as in a configuration comprising one or more loops, curls or sub-circles. FIG. 6 illustrates example shapes for the frame that include one or more loops, curls, or sub-circles. The curls may be integrally connected in a linear fashion, as shown in Examples B, C, D, and E, or in a radial fashion, as shown in Examples F and G. The curls may turn in the same direction, as shown in Examples B and E, or in alternating directions as shown in Examples C and D. The curls may also overlap, as shown in Examples A, B, and E. The opposing ends of the elastic wire may be adapted to avoid tissue irritation and scarring. For example, the ends may be soft, blunt, inwardly directed, joined together, or a combination thereof. The frame may also include a one or more circles or ovals arranged in a two-dimensional or a three-dimensional configuration. FIG. 7 illustrates example shapes for the frame that include one or more circles or ovals arranged in a two-dimensional or a three-dimensional configuration. The frame may include a number of concentric circles, as shown in Example A, or a number of concentric ovals, as shown in Examples B and C. Each of the circles or ovals may be closed, and the circles or ovals may be joined at a common connecting point. Alternatively, one or more of the circles and ovals may be open. The circles and ovals may also be connected at a number of connecting points. The frame may also include a number of overlapping circles or ovals. The overlapping circles or ovals may each be substantially the same size, as shown in Example D, or the circles or ovals may vary in size, as shown in Examples E and F. Circles may also be combined with ovals, depending on the embodiment. Further, the frame may be an open-ended spiral, as shown in Example G, or the frame may be a spiral having closed ends.

Combination of the Components

The vesicle retention frame is associated with the drug reservoir portion to form the drug delivery device. A variety of different associations are envisioned. For example, the drug reservoir portion may be attached to an intermediate region of the vesicle retention frame. More specifically, the vesicle retention frame may have a first end, an opposing second end, and an intermediate region therebetween, and the drug reservoir portion may have first and second end portions that are attached to the intermediate region of the vesicle retention frame. The end portions of the drug reservoir may terminate at the vesicle retention frame, the end portions may overlap the vesicle retention frame, or a combination thereof. The drug reservoir portion may be oriented with reference to the retention frame such that the drug reservoir portion lies within the perimeter of the retention frame, beyond the perimeter of the retention frame, or a combination thereof. Additionally, a number of drug reservoir portions may be associated a single retention frame, depending on the configuration of the device.

Figure 8:
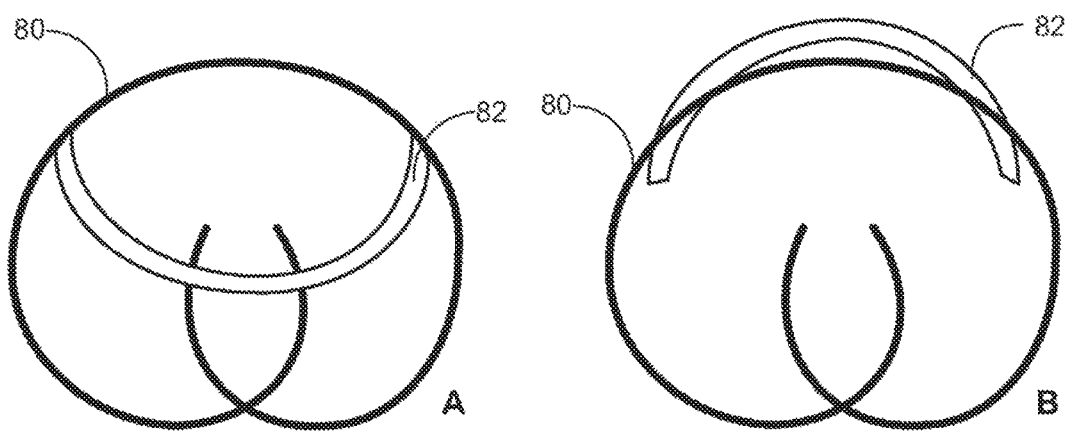
FIG. 8 illustrates examples embodiments of a pretzel shaped retention frame having one or more drug reservoirs attached at an intermediate region of the retention frame.
Figure 8:
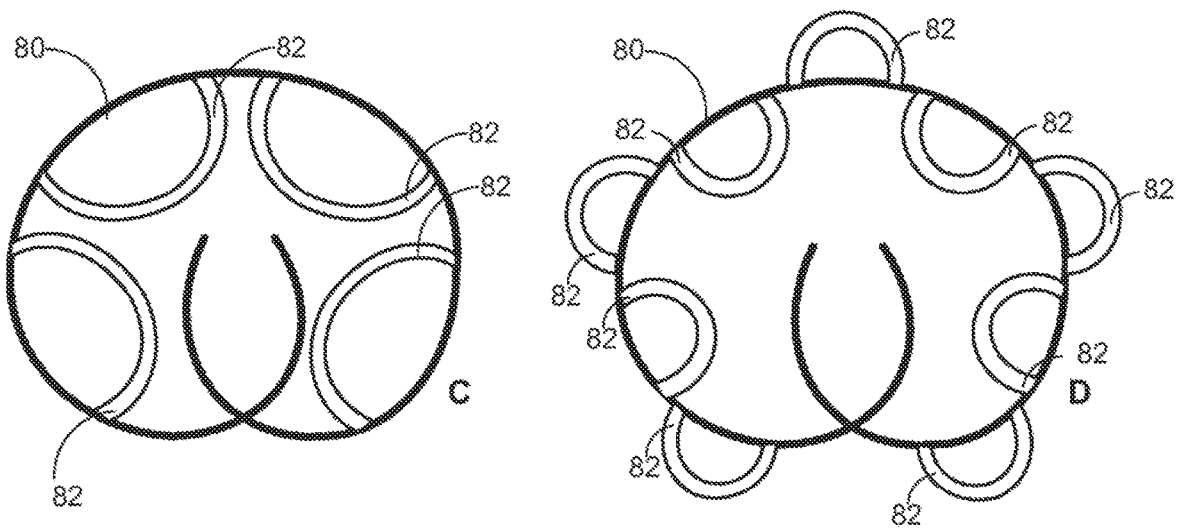

FIG. 8 illustrates example embodiments of a pretzel shaped retention frame 80 having one or more drug reservoirs 82 attached at an intermediate region of the retention frame 80. Specifically, Example A illustrates an embodiment having one drug reservoir, wherein the drug reservoir lies within the perimeter of the retention frame and has end portions attached to the intermediate region of the retention frame terminating at the retention frame. Example B illustrates an embodiment having one drug reservoir, wherein the drug reservoir lies outside of the perimeter of the retention frame and has end portions attached to the intermediate region of the retention frame slightly overlapping the retention frame. Example C illustrates an embodiment having a number of drug reservoir portions, each drug reservoir portion lying within the perimeter of the retention frame, and Example D illustrates an embodiment having a number of drug reservoir portions, some of the drug reservoir portions lying within the perimeter of the retention frame and some of the drug reservoir portions lying outside of the of the perimeter of the retention frame.

Figure 9A:
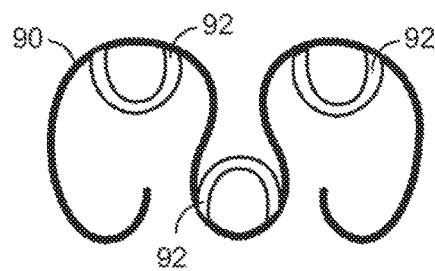
FIGS. 9A-9B show another embodiment of a retention frame having a number of drug reservoir portions attached at an intermediate region of the retention frame, with FIG. 9A illustrating the device shown in a relatively expanded shape and FIG. 9B illustrating the device in a relatively lower profile shape within a catheter.
Figure 9B:
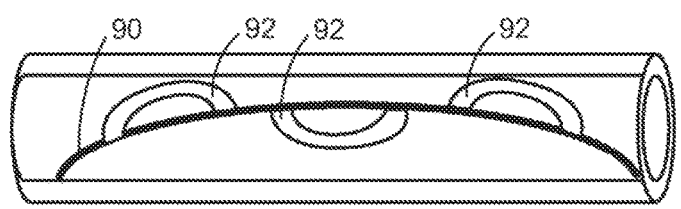

In one embodiment, multiple drug reservoir portions are associated with a single retention frame. For example, FIG. 9 shows an embodiment of a retention frame 90 having a number of drug reservoir portions 92 attached at an intermediate region of the retention frame 90, with the device shown in a relatively expanded shape in FIG. 9A and the device shown in a relatively lower profile shape within a catheter in FIG. 9B. Including multiple discrete drug reservoir portions may facilitate delivering multiple different drugs into the body, delivery different forms of drugs into the body, delivery drugs at varying rates into the body, or a combination thereof.

Figure 10:
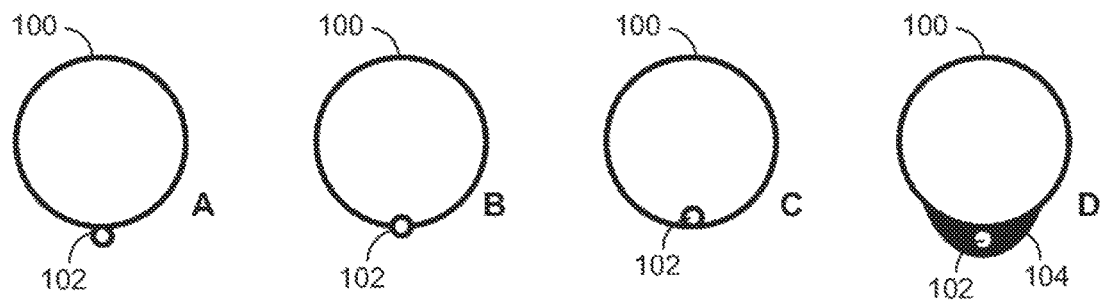
FIG. 10 illustrates cross-sectional views of example embodiments of a drug delivery device having a drug reservoir portion substantially aligned with a retention frame.
Figure 10:
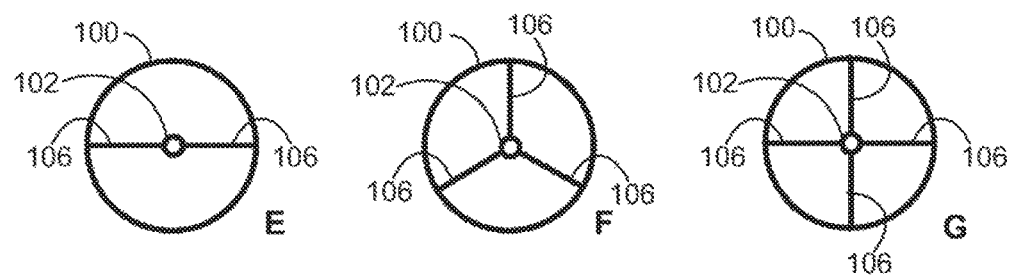

In other embodiments, the drug reservoir portion and the vesicle retention frame portion may be at least partially aligned. In other words, the drug reservoir portion may extend along at least a portion of the length of the retention frame portion, substantially parallel or coincident with the retention frame portion. For example, the drug reservoir portion may extend along the entire length of the retention frame portion. Examples of such embodiments are shown in FIG. 10, which illustrates several alternative embodiments in cross-section. Although only one cross-section is shown, the device may have the same cross-section, or a similar cross-sectional configuration, along substantially the entire length of the device or along a substantial portion of the device. The retention frame may comprise an elastic wire 102 associated with the tube 100 of the drug reservoir portion, as shown in Examples A, B, C, and D. The elastic wire 102 may extend along an exterior surface of the tube 100 as shown in Example A. The elastic wire 102 also may extend along an interior surface of the tube 100, as shown in Example C. The elastic wire 102 may also extend through the surface of the tube 100, as shown in Example B. In embodiments, the tube 100 may be strengthened near the elastic wire 102 with a reinforcement area 104, which may reduce the risk of the elastic wire 102 tearing through or becoming detached from the tube 100. For example, the reinforcement area 104 may be an area of additional silicone. The elastic wire 102 may also be positioned within the interior of the tube 100 supported by a web 106, as shown in Examples E, F, and G. In addition to supporting the elastic wire 102, the web 106 may partition the tube 100 into multiple compartments. For example, the web 106 partitions the tube 100 into two compartments in Example E, three compartments in Example F, and four compartments in Example G, although other configurations are possible. The web 106 may be perforated or otherwise non-continuous so that the compartments are in communication with each other. Alternatively, the web 106 may be relatively continuous such that the compartments are segregated from each other. In such embodiments, the discrete compartments may form different reservoirs that may be suited for holding different drug formulations. The web 106 may be formed from the same material as the tube, or from a material having a different permeability to water or urine, depending on the embodiment.

Figure 11:
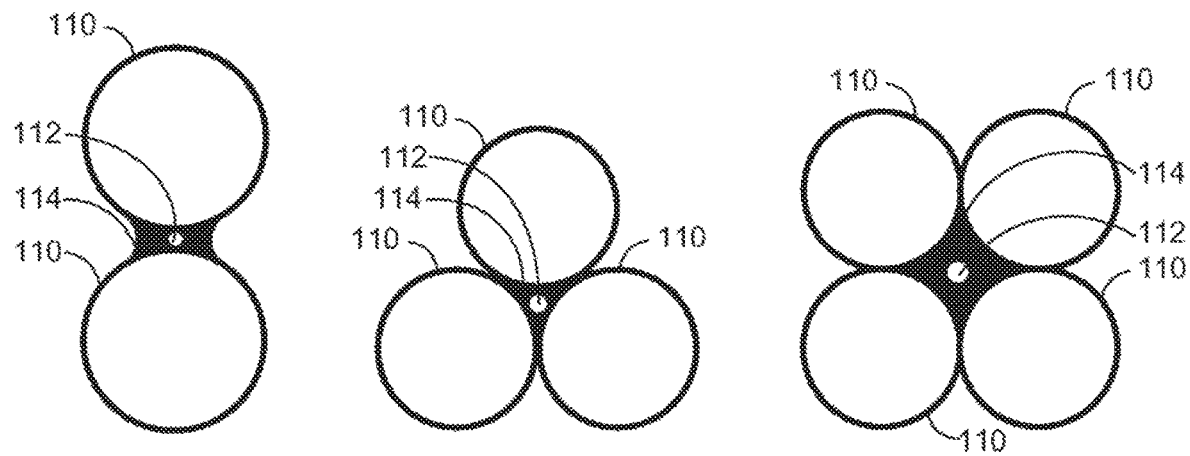
FIG. 11 illustrates cross-sectional views of example embodiments of a drug delivery device having a number of drug reservoir portions substantially aligned with a retention frame.

In still other embodiments, the elastic wire may be associated with multiple tubes, extending along or between the tubes. Examples of such embodiments are shown in FIG. 11, which illustrates several alternative embodiments in cross-section. In such embodiments, multiple discrete tubes 110 may be joined together by a reinforcement area 114, with the elastic wire 112 embedded in the reinforcement area 114, as shown in Examples A, B, and C. The number of tubes 110 may vary. For example, two tubes 110 are shown in Example A, three tubes 110 are shown in Example B, and four tubes 110 are shown in Example C, although additional tubes may be provided in embodiments not shown. In such embodiments, the same or different drug formulations may be loaded in the discrete tubes 110. The discrete tubes 110 may also be formed from the same or different materials of construction, such as materials that differ in permeability to urine or other aqueous or bodily fluids.

The embodiments described above may be combined and varied to produce other drug delivery devices that fall within the scope of the present disclosure. For example, the drug reservoir portion may be attached to any portion of the retention frame in any manner, than the intermediate region. Also, the drug reservoir portion may be wrapped around the elastic wire of the retention frame, one or any number of times. It should be noted that the retention frame is generally described as being an elastic wire for the sake of simplicity, and that the elastic wire may be coated with a polymer tubing in any of these embodiments, as described above with reference to FIG. 1. Also, the term "drug reservoir portion" generally refers to the discrete tube that is associated with the retention frame, although this tube may be separated or otherwise partitioned into any number of discrete drug reservoirs, as described above with reference to FIG. 4 and FIG. 11. Providing multiple drug reservoir portions, partitioning a single drug reservoir portion into multiple drug reservoirs, or a combination thereof, may facilitate delivering multiple different drugs into the body, delivery different forms of drugs into the body, delivery drugs at varying rates into the body, or a combination thereof. For example, the device may hold a drug in both a liquid form for earlier release upon implantation and in solid or semi-solid form for later release after the drug is solubilized.

The drug reservoir component can be attached to the vesicle retention frame using essentially any biocompatible material or structure. For example, the drug reservoir portion may be attached to the retention frame using a medical grade silicone adhesive.

Figure 12:
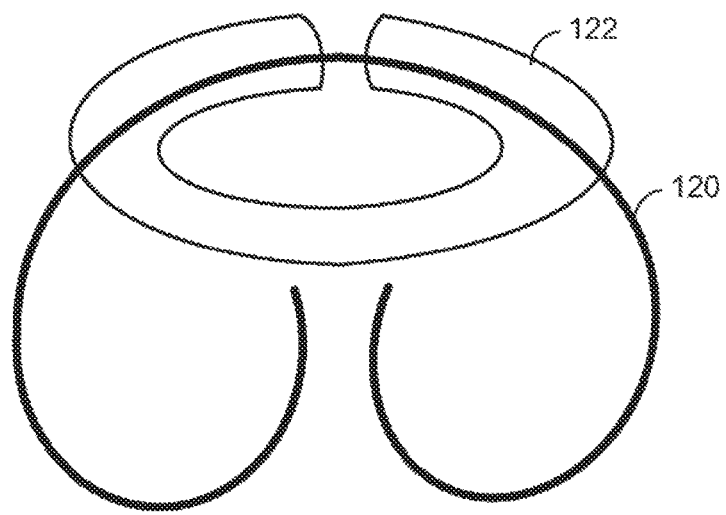
FIG. 12 illustrates an embodiment of a drug delivery device wherein a retention frame component extends through a portion of a drug reservoir component to attach the two components together.

In embodiments, the drug reservoir component may be attached to the vesicle retention frame by at least partially imbedding the elastic wire of the retention frame within the elastomeric tube of the drug reservoir portion. In the embodiment illustrated in FIG. 12, a portion of a pretzel shaped elastic wire 120 extends through first and second ends of a drug reservoir portion 122, although other configurations are possible. In such embodiments, the tubing of the drug reservoir portion may be formed with the wire in it, or the tube may be penetrated by the wire after both parts are formed, to connect them.

In still other embodiments, the drug reservoir portion may be integrally formed with the retention frame. For example, a casting method may be used, which may include pouring a curable silicone into a mold and allowing the silicone to cure. In some such embodiments, the elastic wire may be positioned in the mold along with the silicone.

Further, the drug reservoir portion and the retention frame portion may be the same component in some embodiments. In such cases, the device may comprise a silicone tubing formed in a configuration having a sufficient spring constant to retain the device in the body, as described above. In such cases, attachment may not be necessary.

Other Device Features

The rate and total amount of drug delivered from a single device may depend on, for example, the surface area of the drug reservoir portion, the type and permeability of the materials of construction of the drug reservoir portion, the number of apertures formed through the drug reservoir portion, and the total mass of drug load, among others. Particular target therapeutic dosages and acceptable implant dimensions for a particular body cavity and route of implantation can be selected for different drugs and therapies.

In embodiments, the drug reservoir portion can be partially or wholly coated with a coating or a sheath, which may facilitate controlling the release rate. The coating or sheath may be relatively less permeable to water than the drug reservoir portion. Thus, the coating or sheath may modulate or reduce the water permeability of the drug reservoir portion to control or slow the rate of release of the drug from the device. In some cases, the coating or sheath may be partially permeable to water, in which case the coating or sheath may cover all or a portion of the drug reservoir portion. For example, the coating or sheath may comprise a mesh that covers substantially the entire device. In other cases, the coating or sheath may be substantially impermeable to water, in which case the coating or sheath may cover only a portion of the device body. Regardless, the coating or sheath may reduce or alter the osmotic surface area of the device body. Due to the reduced or altered osmotic surface area, the release rate of drug from the drug reservoir portion may be reduced or altered.

Because the coating or sheath may permit controlling the release rate, the drug reservoir portion may be sized, shaped, and constructed to house a certain drug payload volume, to achieve a certain flexibility or spring constant, or to assume a certain shape during implantation or once implanted, among others. These characteristics of the drug reservoir portion may be selected without regard to how such characteristics affect the release rate, as the release rate may be independently controlled by controlling the osmotic surface area with the coating or sheath. Thus, the release rate may be altered without changing the overall size of the device body, the shape of the device body, or the materials used to form the device body.

In cases in which the drug reservoir portion is formed from silicone tubing, the coating or sheath may be formed from a material that is relatively less permeable to water or urine than silicone. For example, the coating or sheath may be formed from a polymer, parylene, a curable silicone, or another biocompatible coating or sheath material known in the art. In one embodiment, the device body may be formed from silicon tubing, while the sheath may be formed from polyurethane.

The coating or sheath may have be relatively uniform along the device body to facilitate relatively uniform release of the drug from the reservoir. Alternatively, the coating or sheath may vary along the device body, so that certain parts of the device body have higher or lower water permeability relative to other parts of the device body. For example, one or more characteristics of the coating or sheath may vary over the device body to achieve the desired release rate.

Example characteristics of the coating or sheath that may vary include thickness, size, or shape of the coating or sheath; position, location, or orientation of the coating or sheath on the device body; and material used to form the coating or sheath, among others.

Further, multiple coatings or sheaths may be provided along different portions of the device body. In some cases, the multiple coatings or sheaths may correspond to multiple reservoirs formed in the device body, each of the multiple reservoirs containing a different drug. In such cases, the multiple coatings or sheaths may have the same characteristics to permit relatively uniform release of the different drugs from the different reservoirs. Alternatively, the multiple coatings or sheaths may have differing characteristics to permit differing release rates of the different drugs from the different reservoirs. Example coating or sheath characteristics that may differ to vary the release rate include thickness, size, shape, position, and material, among others, as described above. For example, the tube around a first reservoir may be coated with a first coating of a first material and a first thickness, while the tube around a second reservoir may be uncoated, coated with a second (different) coating material, or coated with the first coating material but at a second (different) thickness. Thus, the release rate from the first reservoir may differ from the release rate from the second reservoir.

Figure 13:
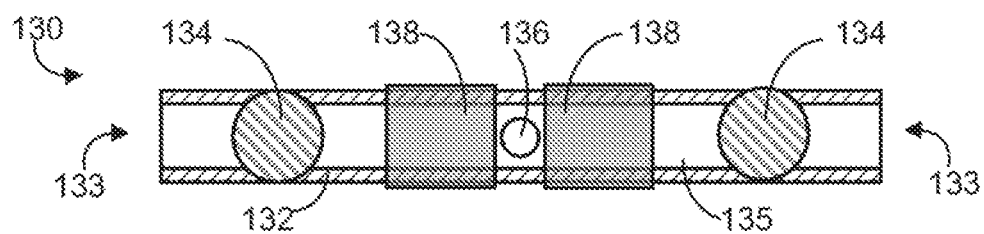
FIG. 13 is a side view of an embodiment of a drug delivery device, illustrating rate controlling coatings or sheaths positioned near a release aperture, with interior components of the device being illustrated with cross-hatching.

In embodiments, the positioning of the coating or sheath about the device body may be selected to augment or otherwise control dissolution of solid or semi-solid forms of the drug. An example is shown in FIG. 13. As shown, the device body 130 may be formed from a tube 132, such as a silicone tube. The tube 132 may have two opposed ends 133. A microsphere 134 may enclose each of the ends 133, and a reservoir 135 may be formed between the ends 133. An orifice 136 formed through the tube 132 may permit releasing a drug from the reservoir 135. To control the release of the drug from the orifice 136, at least one sheath 138 may be positioned about the tube 132. For example, a sheath 138 may be positioned on each side of the tube 132 between the orifice 136 and the end 133. So that the drug does not become stagnated below the sheath 138, the sheath 138 may be spaced inward from the end 133. As shown, the sheath 138 may be relatively closer to the orifice 136 than to the end 133, such as directly adjacent to the orifice 136, although other configurations are possible. Such placement of the sheath 138 may facilitate releasing the drug from the orifice 136, as the positioning may permit water to permeate the tube 132 adjacent to the end 133. As water permeates through the tube 132 adjacent to the end 133, the drug may be driven through the portion of the tube 132 covered by the sheath 138 and out of the orifice 136. Thus, isolation or stagnation of the drug positioned under the sheath 138 may be avoided. Examples 1 and 2, below, provide release rate data for a drug delivery device having a sheath, and also provide example equations for selecting the length of sheath to achieve a desired release rate.

In a preferred embodiment, the tube preferably includes at least one radio-opaque portion or structure to facilitate detection or viewing of the device as part of the implantation or explantation procedure. In one embodiment, the tube is constructed of a material that includes a radio-opaque filler material, such as barium sulfate or another radio-opaque material known in the art.

Silicone tubing may be made radio-opaque (for X-ray imaging or fluoroscopy) by blending radio-opaque fillers, such as barium sulfate or other suitable materials, during the processing of the tubing. Ultrasound imaging can also detect silicone in vivo, but it may suffer from lack of resolution to be able to correctly image the device if the latter is kept small. Fluoroscopy may be the preferred method during deployment/retrieval of the non-resorbable device by providing accurate real-time imaging of the position and orientation of the device to the practitioner performing the procedure.

In one embodiment, the body of the intravesical drug delivery device further includes at least one retrieval feature. The retrieval feature may be a structure that facilitates removal of the device from the body cavity, for example for removal of a non-resorbable device body following release of the drug formulation. Embodiments of retrieval features are described in U.S. patent application Ser. No. 11/463,956, which is incorporated by reference above. In these and in other embodiments, the device may be retrieved using conventional endoscopic grasping instruments, such as alligator forceps, three or four-pronged optical graspers. For example, if the device has an O-shaped or coiled portion, the removal of the device can be facilitated by those grasping instruments.

In embodiments, the device may be designed to administer drugs to achieve an immediate affect during an acute phase and to achieve a prolonged effect during a maintenance phase. For example, the device may have two drug reservoirs or drug reservoir portions, one of which is configured to release a drug relatively quickly after implantation and one of which experiences an induction time before beginning release. To accomplish such a result, the two drug reservoirs or drug reservoir portions may have different configurations, such as different permeabilities, or the two drug reservoirs or drug reservoir portions may store different forms of the drug, such as a liquid form for immediate release and a solid form to be solubilized prior to release. These embodiments can be combined and varied with other embodiments described herein to achieve the desired release profile.

II. Method of Making the Device

Figure 14:
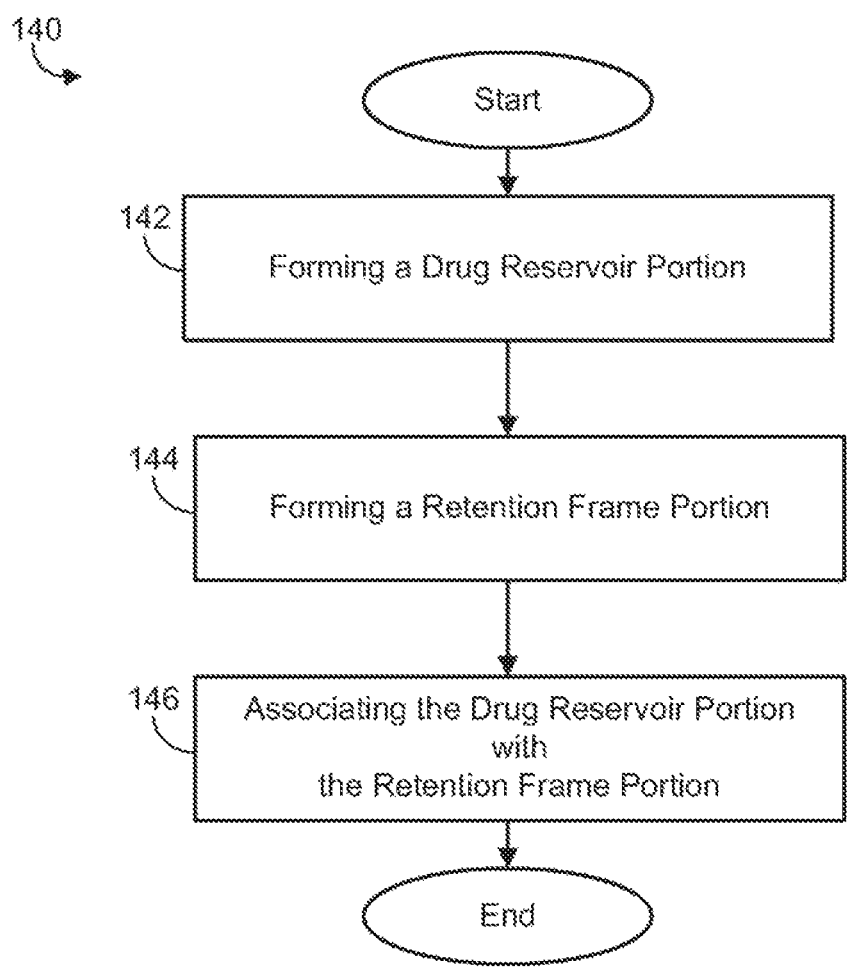
FIG. 14 is a block diagram illustrating an embodiment of a method of making an implantable drug delivery device.

In another aspect, a method of making an implantable drug delivery device is provided. FIG. 14 is a block diagram illustrating an embodiment of such a method 140. In block 142, a drug reservoir portion is formed. In block 144, a vesicle retention frame portion is formed. In block 146, the drug reservoir portion is associated with the vesicle retention frame portion.

In embodiments, forming the drug reservoir portion in block 142 may include one or more of the following sub-steps: forming the drug reservoir tube, forming a relatively solid drug rod, loading the drug rod into the tube, inserting a sealing material into the tube between an end of the drug rod and an end of the tube, and forming one or more apertures in the tube.

The drug reservoir tube may be formed using conventional methods, such as injection molding, compression molding, extrusion molding, transfer molding, insert molding, thermoforming, casting, or a combination thereof. The hollow tube may be formed from a material that is biocompatible, water permeable, elastic, or any combination thereof. For example, the tube may comprise silicone.

The drug rod may be formed by filling a mold with an aqueous solution comprising the drug and allowing a solvent to evaporate from the solution. For example, a lidocaine drug rod may be formed by filling a mold with an aqueous solution of lidocaine, allowing at least a portion of the solvent to evaporate to form a saturated or super saturated solution of the drug, and then crystallizing the resulting gel to form a lidocaine drug rod. A seed crystal may be introduced into the saturated or supersaturated solution to initiate crystal growth and thus precipitation of the drug. In such cases, the evaporation and crystallization steps may be done at one or more controlled temperatures. As another example, lidocaine hydrochloride may be combined, e.g., in a 70:30 mixing ratio, with chondroitin sulfate C, to produce a drug rod with some stiffness to enhance handling of the device, although such a process sacrifices some of the payload of lidocaine hydrochloride. Whether that sacrifice is acceptable depends on the particular device design and application/use In embodiments in which a drug rod is formed, the tube of the drug reservoir portion may or may not serve as the mold. In embodiments in which the tube does not serve as the mold, the completed drug rod may be loaded into the tube by manipulating the drug rod into the tube using, for example, a guide wire and/or tweezers.

In embodiments in which the drug formulation is in liquid form, the drug formulation may be loaded into the drug reservoir portion through the apertures or through another opening that it subsequently sealed. However, it may be relatively easier to load the drug in solid or semi-solid form, and such forms may further reduce the size of the device, which may facilitate reducing irritation to surrounding tissue.

The one or more apertures may be formed in one or more of the following: the side wall of the tube, an end of the tube, or a combination thereof. The one or more apertures may be formed by laser drilling one or more holes in the tube. The laser drilling may occur before or after the drug rod is loading into the tube. Alternatively, the apertures may be formed simultaneously with the device body, such as by molding with an indenter as described in U.S. Pat. No. 6,808,522 to Richards et al.

In embodiments, forming the drug reservoir portion in block 142 may comprise forming multiple different drug reservoirs in a single drug reservoir portion. In such embodiments, one or more partitioning structures may be inserted into and positioned within the tube, for example using a guide wire. In cases in which multiple reservoirs and partitions are used, the installation of the partition structures may be alternated with the loading of the drug formulation. The position of the partition structure may be secured using adhesive or by frictional engagement with the tube, such as in cases in which the partition has a slightly larger outer diameter than the inner diameter of the tube.

In embodiments, forming the drug reservoir portion in block 142 may further include associating one or more release controlling structures with the drug reservoir portion. For example, a sheath or coating may be placed over at least a portion of the surface of the tube to control the rate of release of the drug. Additionally, a degradable membrane may be positioned over or in one or more of the apertures to control the initial time of release of the drug therethrough. The degradable membranes may be formed by microinjecting or inkjet printing a fluid to form a membrane at one end of the aperture, e.g., in/on the outer surface opening in the tube. For example, the fluid may be a solution comprising a resorbable material dissolved in a solvent, a suspension comprising a resorbable material in a nonsolvent, or a liquefied resorbable material. Also, the drug reservoir portion may be formed from a drug polymer composite designed to release at a known rate.

In embodiments, the step of forming a vesicle retention frame portion may vary depending on the material used to form the frame. In embodiments in which the retention frame comprises an elastic wire formed from a superelastic alloy or shape memory material, for example, the step of forming the vesicle retention frame may comprise forming the elastic wire into the relatively expanded shape and "programming" the shape into the elastic wire via heat treatment. For example, the retention frame 14 shown in FIG. 1 may be formed by forming the elastic wire 16 into a pretzel shape and heat treating the elastic wire 16 at a temperature over 500° C. for a period over five minutes. Also in such embodiments, forming the vesicle retention frame portion may include one or more of the following: forming a polymer coating or sheath over the elastic wire, smoothening the ends of the elastic wire, and applying a radio-opaque material to at least a portion of the elastic wire. In such embodiments the polymer sheath, the radio-opaque material, and the smoothening material may be applied to the elastic wire in any order. For example, a platinum wire may be wound around ends of the elastic wire to improve the radio-opacity of the device to x-ray, the ends of the elastic wire may be smoothened with an ultraviolet-curable epoxy, and the polymer sheath or coating may be placed over the elastic wire.

In embodiments in which the retention frame comprises a low modulus elastomer, the step of forming the vesicle retention frame may comprising forming one or more windings, coils, loops or spirals in the frame so that the frame functions as a spring. For example, the retention frame may be formed by extrusion, liquid injection molding, transfer molding, or insert molding, among others.

In embodiments, the step of associating the drug reservoir portion with a vesicle retention frame portion may comprise orienting the drug reservoir portion with reference to the retention frame portion and applying an adhesive therebetween. The drug reservoir portion may be oriented in a variety of orientations as described above. In other embodiments, the step of associating the drug reservoir portion with the vesicle retention frame portion may comprise inserting an elastic wire of the retention frame portion at least partially through the drug reservoir portion. In still other embodiments, the step of associating the drug reservoir portion with the vesicle retention frame portion may comprise integrally forming the two portions together.

III. Use and Applications of the Device

The intravesical drug delivery device may be used to deliver drug locally to essentially any body cavity site. In a preferred embodiment, the body cavity may be the bladder of a male or female human patient in need of treatment. For example, the intravesical drug delivery device may be used in the treatment of interstitial cystitis, radiation cystitis, overactive bladder syndrome, or bladder cancer, although the device also may deliver drug to the bladder for the treatment of other conditions. In other embodiments, the present intravesical devices may be used in other body cavities of a patient. For example, the small devices may be implanted in a space in the vagina, a gastric cavity, the peritoneal cavity, or an ocular cavity.

In one embodiment, the intravesical drug delivery device is implanted into a patient's bladder to locally deliver a local anesthetic agent for management of pain associate arising from any source. For example, it may be pain from any disease or disorder in genitourinary tissues, pain stemming from any bladder catheterization procedure itself, e.g., post-operative catheterization.

The device may be implanted in the bladder of a patient by any suitable lumen device, generally referred to herein as a catheter, urethral catheter, or cystoscope, as known in the art. These terms are used interchangeably herein, unless otherwise expressly indicated. The catheter may be a commercially available device or one specially adapted to accommodate an embodiment of the present drug delivery devices.

Figure 15:
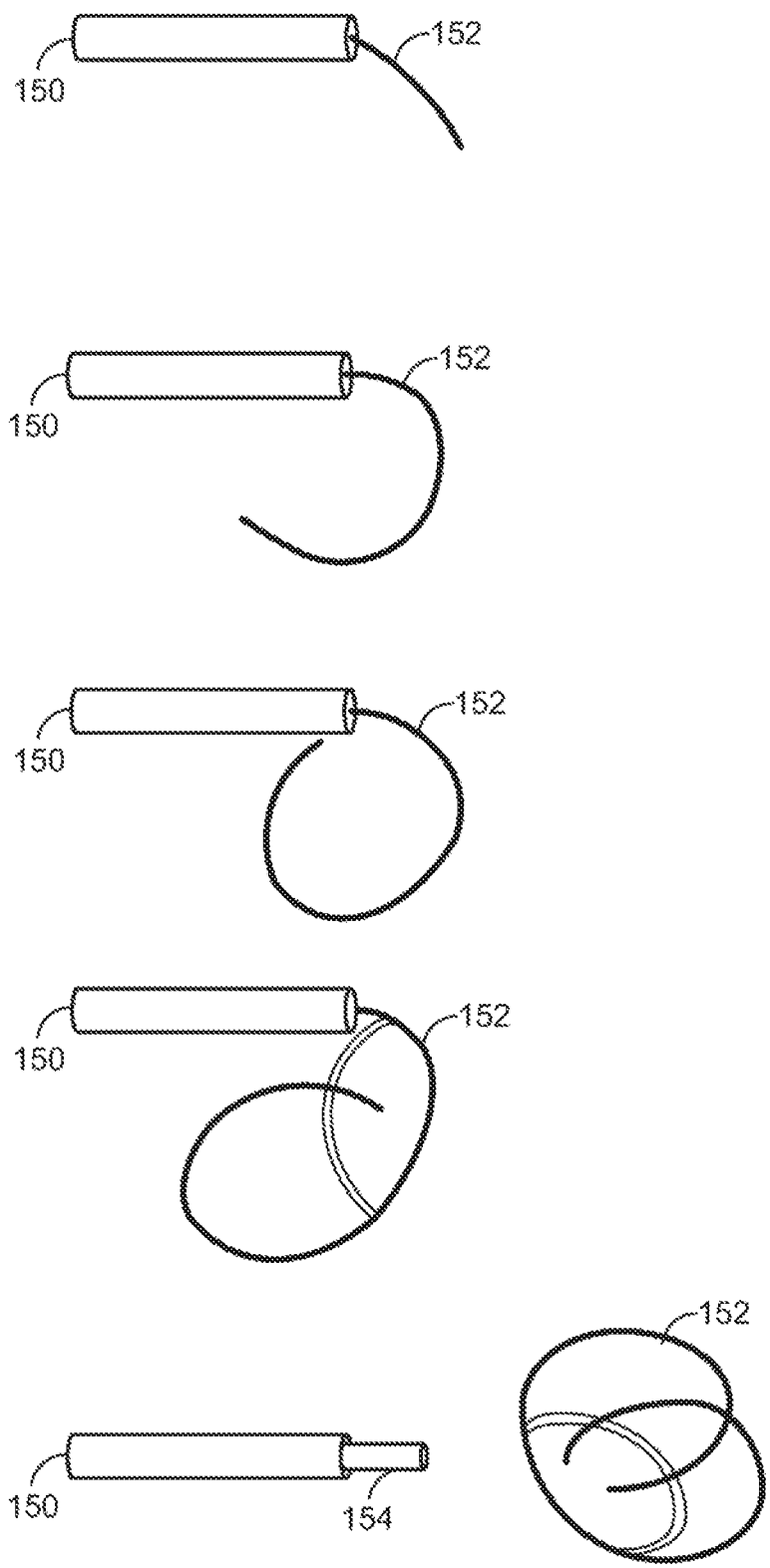
FIG. 15 illustrates a method of implanting an intravesical drug delivery device.

In one example, a method of implanting an intravesical drug delivery device in a body cavity comprises passing the intravesical drug delivery device through a catheter in a relatively low-profile shape, and releasing the device from the catheter into the body cavity, the device assuming a relatively expanded shape once the device emerges from the catheter for retention in the body cavity. In embodiments, the relatively lower profile shape may be a relatively linear, folded, expanded, or compressed form. The catheter may be inserted into the urethra to permit access to the bladder. FIG. 15 illustrates an embodiment of the releasing step of the method. As shown in FIG. 15, the device 152 may be pushed through a catheter 150 using a stylet 154. As shown, the device 152 changes shape as it emerges from the catheter 150, returning to the relatively expanded shape for retention in the bladder. U.S. Pat. No. 6,139,535 also describes a method and apparatus for placement of a medical device in the bladder through the urethra.

In embodiments, the intravesical drug delivery device comprises a drug in a relatively solid form, such as a drug rod or a powder form. Elution of drug from the device occurs upon dissolution of the drug rod. That is, as the drug contacts and becomes solubilized in bodily fluid that enters the device, the dissolved drug diffuses or flows under osmotic pressure from the implanted device. For example, the device may be delivered into the bladder, in which case the drug may be solubilized upon contact with urine in the bladder.

In one embodiment, the intravesical drug delivery device is non-resorbable or otherwise needs to be removed following implantation. In one such a case, the method described in the preceding paragraph further includes removing the intravesical drug delivery device from the body cavity following release of the drug. Specialized retrieval devices are known in the art, or can readily be produced, for this purpose. For example, U.S. Pat. No. 5,499,997 describes an endoscopic grasping method and apparatus.

The device may be used to deliver drugs locally to the bladder as an alternative to systemic delivery, which may be desirable in cases in which systemic delivery may cause undesirable side effects or result in insufficient bioavailability of the drug.

The present intravesical drug delivery device treatment method provides extended, continuous, intermittent, or periodic release of a desired quantity of drug over a desired (predetermined) period of time. In one embodiment, the device can deliver the desired dose of drug over an extended period of time, e.g., 24 hours, 5 days, 7 days, 10 days, 14 days, or 20, 25, 30, 45, 60, or 90 days, or more. The rate of delivery and dosage of the drug can be selected depending upon the drug being delivered and the disease/condition being treated. The use of different degradation rates and/or excipient materials, along with varying the number and size of apertures in the device, can be used to tailor the device to have different release kinetics.

In a preferred embodiment, the device is administered to (i.e., implanted into) the bladder of a patient and delivers in a controlled manner a drug formulation to the bladder. In particular embodiments, the drug formulation includes one or more drugs useful in the treatment of overactive bladder syndrome, bladder cancer, interstitial cystitis, or pain relief.

For example, the device may be used to deliver lidocaine locally to the bladder over an extended time period, such as a period of more than one day. Advantageously, the device enables the delivery, of lidocaine for example, to the bladder to provide an increase in the local concentration of lidocaine in the bladder tissue without producing high systemic levels.

Figure 16:
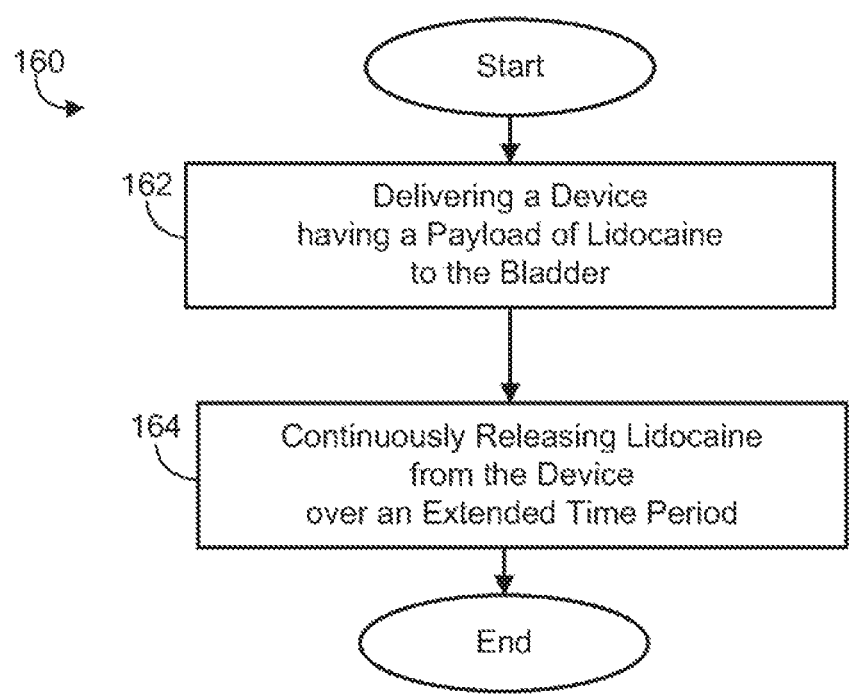
FIG. 16 is a block diagram illustrating a method of delivering lidocaine to the bladder.

FIG. 16 is a block diagram illustrating a method 160 of delivering lidocaine to the bladder. In block 162, a device having a payload of lidocaine is delivered to the bladder. In block 164, the lidocaine is continuously released from the device over an extended period of time. In such embodiments, the device may be an embodiment of the device described above, or the device may be any other device. In embodiments, the payload of lidocaine may be in the range of about 50 mg to about 100 mg. The extended period of time may be in the range of about one day to about fourteen days, for example. Such a method may achieve a sustained level of lidocaine in the urothelium of the bladder.

Advantageously, the sustained level of lidocaine in the urothelium achievable with the present devices and methods can exceed the level that is generally considered to be tolerable systemically. High local concentrations of drug are provided without significant systemic concentrations. This enables the effective use of a relatively small payload of lidocaine to create a therapeutically effective concentration of lidocaine in the urothelium. The urothelium lidocaine concentration may exceed the concentration that could be obtained systemically without causing systemic effects. The urothelium lidocaine concentration may also exceed the concentration that could be obtained via instillation, and further, the high initial peak concentration associated with instillation may be avoided. The small payload may facilitate device safety, as the payload may be sufficiently small to avoid undesirable systemic effects even in the event of device failure. Yet, the small payload may create an effective concentration of lidocaine in the urothelium, due to the local nature of the delivery. See Example 8 below.

In embodiments, the method may delivery the lidocaine without regard to the pH of the urine. For example, the lidocaine need not be administered with a buffering agent, such as sodium bicarbonate. See Example 9 below.

In embodiments, the method may deliver the lidocaine in relatively solid form, which may permit reducing the size of the device to avoid bladder irritation and patient discomfort.

In embodiments, (1) delivering a device having a payload of lidocaine to the bladder may comprise delivering a device to the bladder that has first and second payloads of lidocaine; and (2) continuously releasing the lidocaine from the device over an extended period of time may comprise initiating release of the first payload of lidocaine and subsequently initiating release of the second payload of lidocaine. The first payload may be adapted for relatively quick release, while the second payload may be adapted for more continuous release. For example, the first payload may be in liquid form while the second payload may be in solid form. As another example, the first payload may be housed in a relatively fast-acting osmotic pump, such as a silicone tube having a relatively thinner wall, while the second payload may be housed in an osmotic pump that experiences an initial delay or induction time before releasing, such as a silicone tube having a relatively thicker wall. Thus, the method may continuously release lidocaine into the bladder during an initial, acute phase and during a maintenance phase. Such a method may compensate for an initial induction time of the device, as described below with reference to Example 8.

The present invention may be further understood with reference to the following non-limiting examples.

EXAMPLE 1

Design of a Tubular Osmotic Pump

Described below is the design of a tubular osmotic pump made of silicone. Other biocompatible polymer tubes such as polyurethane can be used depending on the permeability to water (and drug) and mechanical properties. Design equations for the tubular osmotic pump permit obtaining the desired drug payload and release rate. Tube thickness is related to mechanical integrity and water permeability. Tube inner diameter and tube wall thickness determine the drug payload and outer diameter of the tube. Tube length affects both drug payload as well as the macro size or loop diameter of the tubular osmotic pump. Osmotic surface area over which water or urine can permeate through the tube is affected by tube outer diameter and tube length. These parameters influence the overall performance of the osmotic pump.

The tubular osmotic pump holds a drug on an interior reservoir, and is capable of transfer the drug to an outside medium. Parameters of the tubular osmotic pump are defined below.

C: instantaneous drug concentration in the device reservoir
ρ: drug density
S: drug solubility
d: tube inner diameter
h: tube wall thickness
D: diameter of macro loop made of tube
L: tube total length, L=πD
$L_n$: tube length without permeation blocking sheath
Ls: tube length with permeation blocking sheath, $L_s = L - L_n$
V: volume of drug reservoir, $$V = \frac{\pi d^2 L}{4}$$

m: instantaneous drug amount remaining in the device reservoir, $$m = CV = C\frac{\pi d^2}{4}L$$

$m_p$: total drug payload, $$m_p = \rho V = \rho \frac{\pi d^2}{4} L$$

ΔΠ: osmotic pressure difference between the inside and outside of the tube
$\Delta\Pi_S$: osmotic pressure difference at saturation between the inside and outside of the tube k: permeability coefficient for solvent transport
A: osmotic surface area for water permeation, $A = \pi(d+h)L_n$
$t_z$: duration of zero order release $$\frac{dm}{dt}:$$

the rate of drug mass change in the reservoir, $$\frac{dm}{dt} = -kA\frac{\Delta\Pi}{h}C$$

$\dot{m}_z$: zero order release rate.

$$\dot{m}_z = -\frac{dm}{dt}\bigg|_{zero} = kA\frac{\Delta\Pi_S}{h}S$$

$m_z$: amount released during zero order release, $m_z = \dot{m}_z \cdot t_z$
The parameter 'dm/dt' is defined as the rate of drug mass loss in the device reservoir since 'm' indicates the instantaneous drug amount remaining in the device reservoir. The minus sign in the expression 'dm/dt' reflects the fact that the device will lose its drug by osmotic release once the device is immersed in water or urine. When the osmotic pressure of the surrounding medium is small enough compared to the osmotic pressure of the formulation inside the drug reservoir, van't Hoff's law can be used to obtain:

$$\frac{\Delta\Pi_C}{\Delta\Pi_S} = \frac{C}{S} \qquad (1.1)$$

where the proportional relationship between the osmotic pressure and concentration is used.

The drug release rate from the device remains constant at the initial time period when the concentration inside the drug reservoir is the solubility of drug loaded. The amount of drug released during this initial 'zero-order release period' can be expressed as $$m_z = \left(1 - \frac{S}{\rho}\right)m_p \qquad (1.2)$$

The drug release rate decreases after the zero-order release period as the drug concentration inside the reservoir becomes reduced. The rate of drug mass change (dm/dt) in the reservoir can still be expressed in terms of zero order release rate ($\dot{m}_z$):

$$\frac{dm}{dt} = -kA\frac{\Delta\Pi}{h}C = \left(-kA\frac{\Delta\Pi_S}{h}S\right)\frac{C}{S}\frac{\Delta\Pi}{\Delta\Pi_S} = -\dot{m}_z\frac{C^2}{S^2} \qquad (1.3)$$

The expressions for the amount of drug remaining in the reservoir (m) and the rate of drug mass change (dm/dt) are different for two time periods, the zero order release period and the non-zero order release period. The expressions for the zero-order release period ($0 \le t \le t_z$) are:

$$m = m_p - \dot{m}_z t \quad (1.4)$$

$$\frac{dm}{dt} = -\dot{m}_z \quad (1.5)$$

Eq. (1.3) may be integrated to find the expressions for the non-zero order release period (t≤$t_z$). Drug concentration (C) and drug mass (m) are time-dependent variables and are related by $$m = CV \quad (1.6)$$

After combining Eq. (1.6) with Eq. (1.3), Eq. (1.3) may be integrated from $t_z$ to t to obtain $$\int_{SV}^{m} m^{-2} dm = \int_{t_z}^{t} -\frac{\dot{m}_z}{(SV)^2} dt \quad (1.7)$$

Drug mass remaining inside the reservoir at time t (≥$t_z$) can be expressed as $$m = \frac{S}{\rho} m_p \left[ 1 + \frac{\rho}{S} \frac{\dot{m}_z}{m_p}(t - t_z) \right]^{-1} \quad (1.8)$$

and $$\frac{dm}{dt} = -\dot{m}_z \left[ 1 + \frac{\rho}{S} \frac{\dot{m}_z}{m_p}(t - t_z) \right]^{-2} \quad (1.9)$$

where $$t_z = \left(1 - \frac{S}{\rho}\right) \frac{m_p}{\dot{m}_z} \quad (1.10)$$

The drug mass in the device reservoir beyond $t_z$ can be expressed as $$m = \alpha m_p \; (\alpha \leq 1) \quad (1.1)$$

where α is the ratio parameter indicating remaining drug mass compared to the initial loading (for example, if α is 0.05, then 5% of the total payload remains in the device or 95% of the total loading is released out). Substituting Eq. (1.11) into Eq. (1.8) gives the time t as $$t = t_z + \frac{m_p}{\dot{m}_z}\left(-\frac{S}{\rho} + \frac{1}{\alpha}\frac{S^2}{\rho^2}\right) = \frac{m_p}{\dot{m}_z}\left(1 - 2\frac{S}{\rho} + \frac{1}{\alpha}\frac{S^2}{\rho^2}\right) \quad (1.12)$$

where $t_z$ is replaced by Eq. (1.10). Eq. (1.12) reveals that $$\frac{m_p}{\dot{m}_z}$$

is the factor determining the delivery time scale. This result implies that total payload and initial zero order release rate decides the overall behavior of drug release profile over time.

EXAMPLE 2

Comparison of Release Profiles for Differing Devices

Figure 17:
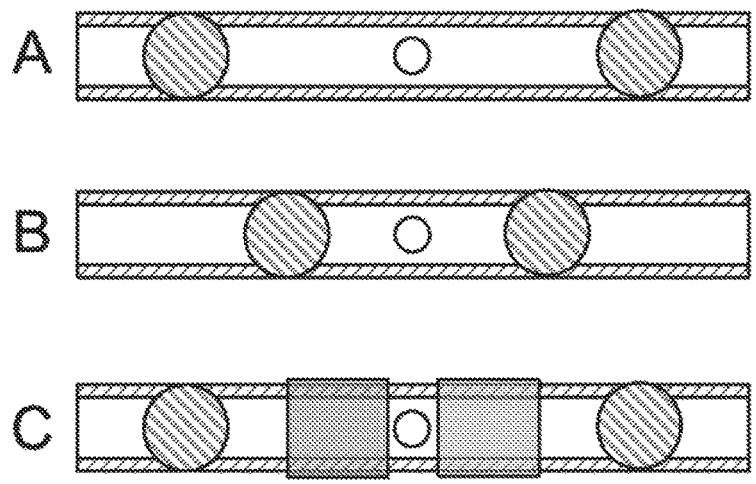
FIG. 17 illustrates cross-sectional views of three different embodiments of a drug delivery device.
Figure 18:
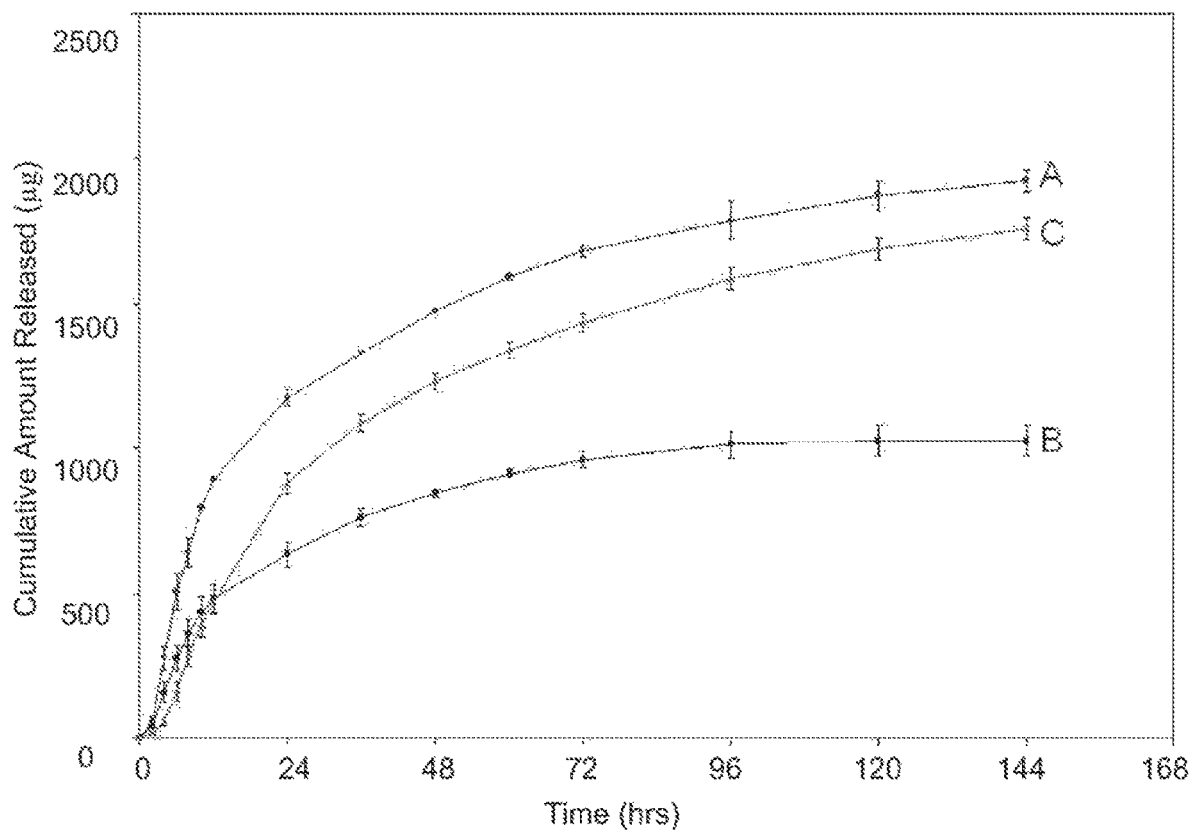
FIG. 18 is a graph illustrating in vitro drug release profiles for the three embodiments of the drug delivery device shown in FIG. 17.

Examples of the application of Eq. (1.12) are presented here. FIG. 17 illustrates three different devices A, B, and C, and FIG. 18 is a graph illustrating in vitro drug release profiles for the three different devices A, B, and C. Each device was a tube that functioned as an osmotic pump. The tubes were formed from silicone. Each tube defined an interior reservoir, and a volume of lidocaine was loaded into the reservoir. Each tube also defined an exterior osmotic surface area, and an orifice was formed in the osmotic surface area. The orifice permitted releasing the lidocaine from the reservoir under osmotic pressure.

More specifically, Device A was a silicone tube having an osmotic surface area of about 2 cm and a reservoir volume of about 2 mg. Device B was a silicone tube having an osmotic surface area of about 1 cm and a reservoir volume of about 1 mg. Device C was a silicone tube having an osmotic surface area of about 2 cm, one half of which was covered with two polyurethane sheaths near the release orifice, and a reservoir volume of about 2 mg. Due to the sheaths, the effective osmotic surface area of Device C was about the same as the osmotic surface area of Device B, and yet the reservoir volume of Device C was about the same volume as the reservoir volume Device A. For each device, the ends of the silicone tube were sealed with micro spheres, and the reservoir was loaded with lidocaine. In the case of Device C, the sheaths were placed relatively near the orifice to limit isolation of the lidocaine during release.

The devices were then tested in vitro in water at 37° C., and the resulting release profiles were plotted in FIG. 18. Drug payload ($m_p$), zero-order drug release rate ($\dot{m}_z$), and delivery time scale ($m_p/\dot{m}_z$) for each device are shown in Table 1, as relative values with respect to the values for Device A. Because Device B had a length that was about one half the length of Device A, both the drug payload and the zero order release rate for Device B were about half the values of the Device A, which results in the same delivery time scale for Device A and Device B. FIG. 18 shows that overall in vitro release profiles with respect to time were similar for Device A and Device B. Device C had a length that was about the same as the length of Device A, but about one half of the length of Device C was covered with polyurethane sheaths to reduce or minimize water permeation. Thus, the zero order release rate for Device C was about half the zero order release rate for Device A. Therefore, the delivery time scale of Device C was about twice that of Device A. FIG. 18 shows that the drug release for Device C is twice as slow as that for Device A.

TABLE 1

Comparison for three devices marked as A, B, and C shown in FIG. 17.

| | Variable | | |
|---|---|---|---|
| Device | Drug payload ($m_p$) | Zero order release rate ($\dot{m}_z$) | Delivery time scale ($m_p/\dot{m}_z$) |
| A | 1 | 1 | 1 |
| B | ½ | ½ | 1 |
| C | 1 | ½ | 2 |

EXAMPLE 3

Selection of Device Characteristics to Achieve a Desired Release Rate

Listed below are equations that permit selecting device characteristics to achieve a desired release rate. More specifically, the equations may permit determining how much of a device should be covered with a coating or sheath to achieve a certain release rate for a certain payload. The device characteristics may be determined with reference to a control device of control dimensions that releases a control drug payload according to a control release profile during in vitro testing. Once theses control parameters are known, the equations may determine the characteristics of a target device that exhibits a target release rate in comparison to the control device.

For purposes of example, Device A of FIG. 17 was the control device. Device A had a the following design parameters:

Tube inner diameter: $d_o$=0.3048 mm
Tube wall thickness: $h_o$=0.1651 mm
Tube length: $L_o$=2 cm
Payload: $m_{p,o}$=2 mg
Treatment duration: about 3 days A control release rate $m_{z,o}$ for Device A is plotted in FIG. 18. Starting with such parameters on the control device, the equations below permit obtaining device characteristics for a target device that will exhibit a desired delivery rate for a desired payload in comparison to the control device. More specifically, two variables are defined:

a=multiplication factor of the target zero order delivery rate
b=multiplication factors of the target payload, respectively. The definitions yield the desired target condition as follows:

Zero order delivery rate ($\dot{m}_z$): a times increase compared with the base condition Drug payload ($m_p$): b times increase compared with the base condition It is assumed here that drug and tube material remain the same for both the base condition and the target condition. The parameters for the target condition have no subscripts here. The zero-order delivery rate condition gives $$\frac{d+h}{h}L_n = \left(\frac{d_o + h_o}{h_o}L_o\right)a \quad (1.13)$$

and the drug payload condition gives $$d^2L = (d_o^2 L_o)b \quad (1.14)$$

Tube wall thickness can vary, but here it is fixed for simplicity:

$$h = h_0 \quad (1.15)$$

It is noted that a tube wall that is too thin may not have sufficient mechanical integrity while a tube wall that is too thick may experience an undesirably long induction time for initial drug release from the device. Thus, a reasonable range of tube wall thickness may be determined based on the mechanical properties and water permeability of the material used to form the polymer tube.

A silicone tube with an appropriately thin wall may act as a water permeable membrane when a drug is loaded inside the tube. The equations below first consider the case where the water permeable tube is not covered with a polymer sheath. Device A and Device B in FIG. 18 show such a case. Water can permeate into the drug reservoir through the entire length of the tube, and so $$L = L_n \quad (1.16)$$

The quadratic equation for the inner diameter can be obtained from Eq. (1.13) and Eq. (1.14): as:

$$d^2 - \frac{(b/a)d_o^2}{d_o + h_o}d - \frac{(b/a)d_o^2}{d_o + h_o}h_o = 0 \quad (1.17)$$

where one solution is positive and the other is negative. The positive solution is designated as $d_1$, and thus the solution for the tube length is $$L_1 = \frac{d_0^2 L_0 b}{d_1^2} = \frac{d_0 + h_0}{d_1 + h_0}L_0 a \quad (1.18)$$

Thus, the tube inner diameter and tube length can be calculated once the multiplication factors for the delivery rate and the drug payload are chosen. Two examples are shown below in Table 2. For tubes formed from different polymers or holding other drugs. additional in vitro release studies may be performed to obtain base conditions for that specific combination of polymer tube and drug.

TABLE 2

Specifications for two examples of devices for human application

| | Multiplication factor | |
| --- | --- | --- |
| Design parameter | For delivery rate (a): 10 For payload (b): 50 | For delivery rate (a): 20 For payload (b): 200 |
| Tube inner diameter ($d_1$) | 1.1326 mm | 2.1303 mm |
| Tube length ($L_1$) | 7.2418 cm | 8.1885 cm |
| Macro loop diameter ($D_1$) | 2.3051 cm | 2.6065 cm |
| Drug payload ($m_p$) | 100 mg | 400 mg |
| Treatment period | 15 days | 30 days |

As mentioned above, the length covered with sheath is denoted as $L_S$. The previous section corresponds to the case where $L_S$=0, which is often the case as it is usually desirable to reduce the diameter of the device. For example, omitting the sheath may facilitate inserting the device through the working channel of a cystoscope, which may have a diameter of about 2.4 mm of less. Nonetheless, the equations next consider the case where the water permeable tube is at least partially covered with a material that reduces the water permeability of the tube, meaning $L_s$>0. Device C in FIG. 18 show such a case. The Device C may be at least partially coated with a sheath or coating made of a polymer having a relatively low permeability to water, such as polyurethane, which may reduce or minimize water permeation into the tube. A special coating such as parylene may also be used to reduce water permeation. Eq. (1.13) and Eq. (1.14) show that the tube length (L) increases faster than the sheath covered length ($L_n$) as the tube inner diameter (d) deceases ($L \propto 1/d^2$ and $L_n \propto 1/(d+h)$). The length of the portion covered with sheath is $$L_S = L - L_n \quad (1.19)$$

Using Eq. (1.13), (1.14), and (1.19), the length covered with sheath is expressed as $$L_s = \pi D - \frac{(d_o + h_o)L_o a}{d_o\sqrt{(L_o b)/(\pi D)} + h_o} \quad (1.20)$$

or using Eq. (1.18), the following is obtained $$\frac{L_s}{L_1} = \frac{D}{D_1} - \frac{d_1 + h_o}{d + h_o} \quad (1.21)$$

where subscript 1 indicates the case where no sheath is used. The portion of the tube length covered with sheath can be expressed in terms of the tube inner diameter (d) as $$\frac{L_S}{L} = 1 - \frac{a(d_o + h_o)}{bd_o^2}\left(\frac{d^2}{d + h_o}\right) \quad (1.22)$$

or in terms of the loop diameter (D) as $$\frac{L_S}{L} = 1 - \frac{(d_o + h_o)L_o a}{d_o\sqrt{\pi bL_o D} + \pi h_o D} \quad (1.23)$$

EXAMPLE 4

Selecting the Characteristics of an Elastic Wire

Figure 19:
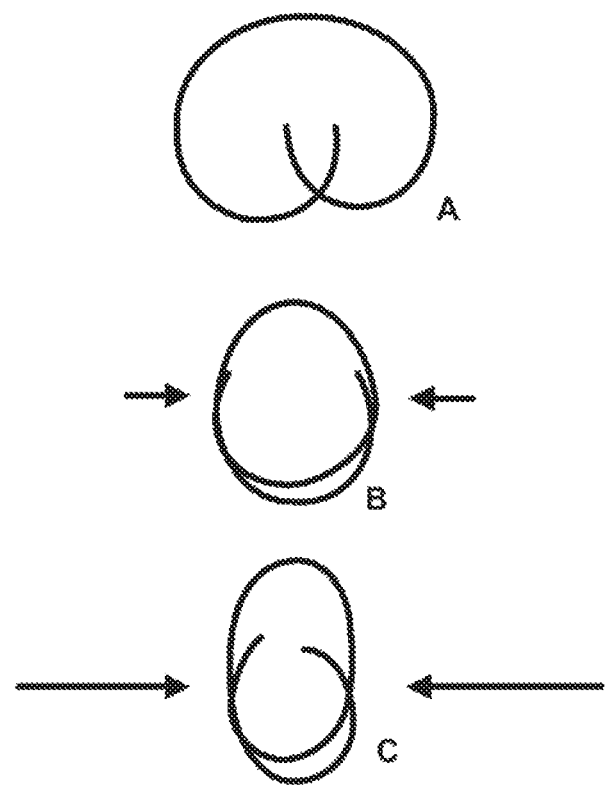
FIG. 19 illustrates an embodiment of a pretzel shaped retention frame, at three different points during a compression test wherein a compressive force was applied to the frame.
Figure 20:
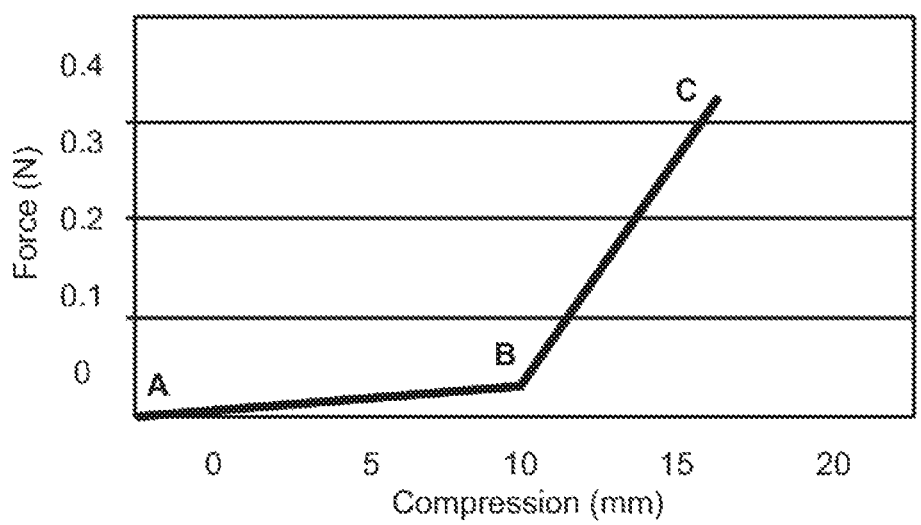
FIG. 20 is a graph illustrating force and displacement data collected during the compression test performed on the device shown in FIG. 19.

A compression test was performed on a pretzel-shaped retention frame, shown in FIG. 19, to demonstrate how various design factors affect the spring constant of a retention frame. The pretzel-shaped elastic wire was made of super-elastic nitinol wire having a diameter of 0.009 inch, or 0.2286 mm. As the compression test was performed, data regarding force and displacement was collected. This data is plotted on the graph shown in FIG. 20.

As a compressive load was applied to the retention frame, the frame deformed from the shape shown in A to the shape shown in B, and finally, to the shape shown in C. Specifically, the three shapes of the device A, B, and C shown in FIG. 19 correspond to the three data points A, B, and C on the graph in FIG. 20.

As shown in FIG. 19, the compressive force was generally absorbed by a larger, common arch of the pretzel-shaped elastic wire as the frame deformed from shape A and shape B. Once the frame assumed shape B, the two semi-circles that make up the elastic wire overlapped. The force/displacement plot demonstrates an increase in slope (approximately 15 times), which was sustained as the frame deformed from shape B to shape C.

The test and subsequent analysis revealed that a small Young's modulus E for low modulus elastomers can be compensated for by one or more of the following: by decreasing the radius of the arch, by increasing the wire diameter, and by having multiple and/or overlapped circles or windings. For example, decreasing the radius of an arch formed by the frame by a factor of two (2) and increasing the diameter of the wire used to form the frame by a factor of two (2) can significantly increase the spring constant by a factor of $2^7$ or 128.

EXAMPLE 5

Sample Spring Constants for Certain Low Modulus Wires

A nitinol wire having a Young's modulus of about 30 GPa, a diameter of about 0.2286 mm, an arc radius of about 1.5 cm, and one coil may have a spring constant of about 3.7 N/m. A polyurethane wire having a Young's modulus of about 25 MPa, a diameter of about 1 mm, an arc radius of about 1 cm, and one coil may have a spring constant of about 3.8 N/m. A silicone wire having a Young's modulus of about 2.41 MPa, a diameter of about 1.2 mm, an arc radius of about 0.75 cm, and two coils may have a spring constant of about 3.6 N/m. A poly(glycerol-sebacate) (PGS) wire having a Young's modulus of about 1.7 MPa, a diameter of about 1.2 mm, an arc radius of about 0.76 cm, and three coils may have a spring constant of about 3.7 N/m.

EXAMPLE 6

In Vitro Delivery of Lidocaine From Various Devices

Figure 21:
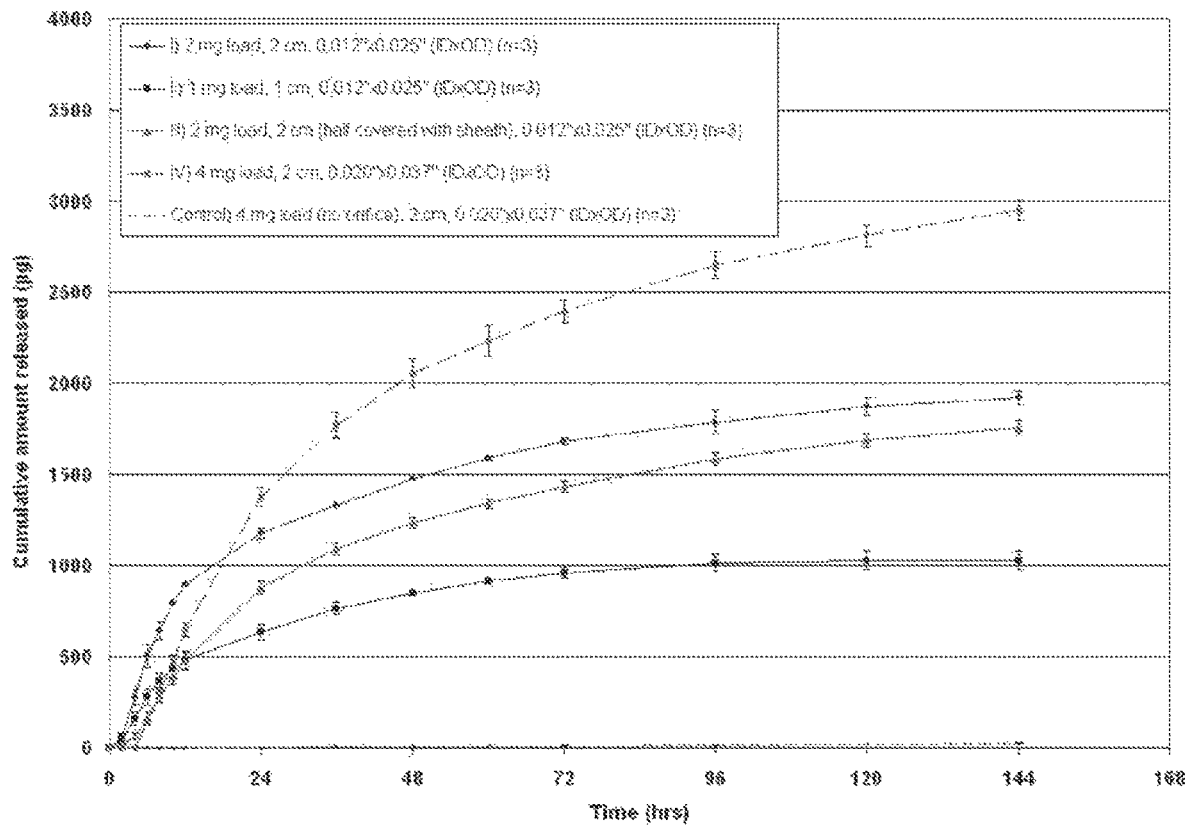
FIG. 21 is a graph illustrating the release of lidocaine over time exhibited in vitro by various implantable drug delivery devices.

An in vitro lidocaine release study was performed with five different devices. Each device was a silicone tube loaded with crystallized lidocaine pieces. Two different sizes of silicone tubes were used. Specifications for the devices are shown in Table 3. Each tube was sealed with stainless steel microballs inserted into the ends. Except for the control device, an orifice was drilled in each tube between the microballs. Each orifice had a diameter of about 50 µm. The diameter was selected to obtain a first-order release profile, based on the results from in vitro release experiments performed with CSC. The device designated Type III in the table has a polyurethane sheath, similar to the one shown in FIG. 13, to reduce water permeation into the device. The device designated Control in the table did not have an orifice. During the experiment, the microballs were pushed outward due to an internal buildup of hydrostatic pressure within the tube. In vitro lidocaine release curves for the devices are shown in FIG. 21.

TABLE 3

Specifications for the devices used for in vitro lidocaine release study

| Type | Payload | I.D. × O.D. (inches) | Tube wall thickness (inches) | Total tube length (cm) |
|---|---|---|---|---|
| I | 2 mg | 0.012 × 0.025 | 0.0065 | 2 |
| II | 1 mg | 0.012 × 0.025 | 0.0065 | 1 |
| III | 2 mg | 0.012 × 0.025 | 0.0065 | 2 (half covered with sheath) |
| IV | 4 mg | 0.020 × 0.037 | 0.0085 | 2 |
| Control | 4 mg | 0.020 × 0.037 | 0.0085 | 2 (no orifice) |

EXAMPLE 7

In Vivo Delivery and Retention of Device in Rabbit Bladder

A vesicle retention frame was made of a Nitinol wire (diameter 0.009 inch) covered with silicone tubing. Platinum wire was coiled at the tip end of the Nitinol wire, and a biocompatible UV epoxy was applied and cured to fabricate a blunt tip end onto the Nitinol wire. The tips are blunt and soft to avoid possible irritations and scarring of the vesicle tissue surface, e.g., the bladder. The coated wire device was in the shape of two overlapping loops with the ends positioned inside of the circle-like outer perimeter defined by the loops. The vesicle retention frame was substantially pretzel shaped.

The retention device was implanted into a rabbit bladder by a 10 Fr. urinary catheter. The shape of the device was chosen as the resistance to the compression increases upon compression of the two loops (i.e., sub-circles). This spring-like feature was intended to prevent collapse of the structure so that it may not enter the urethra. The device immediately returned to its original shape once the compression was removed, due to the superelastic property of Nitinol. Instead of compressing the device into a catheter core, the device was uncurled and pushed through the catheter lumen using a stylet. The device curled back into its original form after emerging from the distal end of the catheter. The device was not excreted from the bladder.

EXAMPLE 8

In Vivo Delivery of Lidocaine in Rabbit Bladder

Drug exposure studies were performed in vivo in rabbit to investigate the absorption of lidocaine by the bladder. The study was conducted with male New Zealand White rabbits. Lidocaine was delivered to some of the rabbits via intravesically implanted drug delivery devices, while instillations were performed on other rabbits for comparative purposes.

For the rabbits treated via instillation, 10 mL of aqueous lidocaine solution was instilled into the bladder. Based on prior clinical studies, the lidocaine dose was either 2 mg or 5 mg per kg of body weight. The solution was instilled using a 10-Fr pediatric Foley catheter inserted through the urethra, and the solution was retained in the bladder for one or two hours. Blood samples were collected at multiple time points before and after instillation. Bladders were collected from the rabbits one day after instillation, and urine samples were also collected at that time.

Rabbits treated via intravesical implant received either a "three-day" device or a "six-day" device. Both devices were comparable in form to the device shown in FIG. 1, each having a pretzel shaped retention frame associated with a silicone drug reservoir component. The drug reservoir component of the three-day device had a tube thickness of about 0.0065 inches, an inner diameter of about 0.012 inches, an outer diameter of about 0.025 inches, and a drug load of about 2 mg of lidocaine, while the drug reservoir component of the six-day device had a tube thickness of about 0.0085 inches, an inner diameter of about 0.020 inches, an outer diameter of about 0.037 inches, and a drug load of about 4 mg of lidocaine. The terms "three-day device" and "six-day device" refer to the configuration of the device and not the length of implantation. For each rabbit, the device was inserted via a modified 10 Fr. urethral catheter using the procedure described above with reference to FIG. 16. The catheter was removed after the device was implanted. Blood samples were collected at multiple points before and after the device implantation. Additionally, x-ray images were taken for one rabbit immediately after implantation, two days after implantation, and nine days after implantation, in both the right lateral recumbent position and the supine position. Multiple x-ray images taken at different times revealed that the device moved freely within the bladder rather than staying in one position. The device was well tolerated by the rabbits over the course of the in vivo study without any health problems. Bladders were collected from the rabbits at multiple time points after implantation, including one day, two days, three days, and six days. Urine samples were also collected at the time the bladders were removed.

Figure 22:
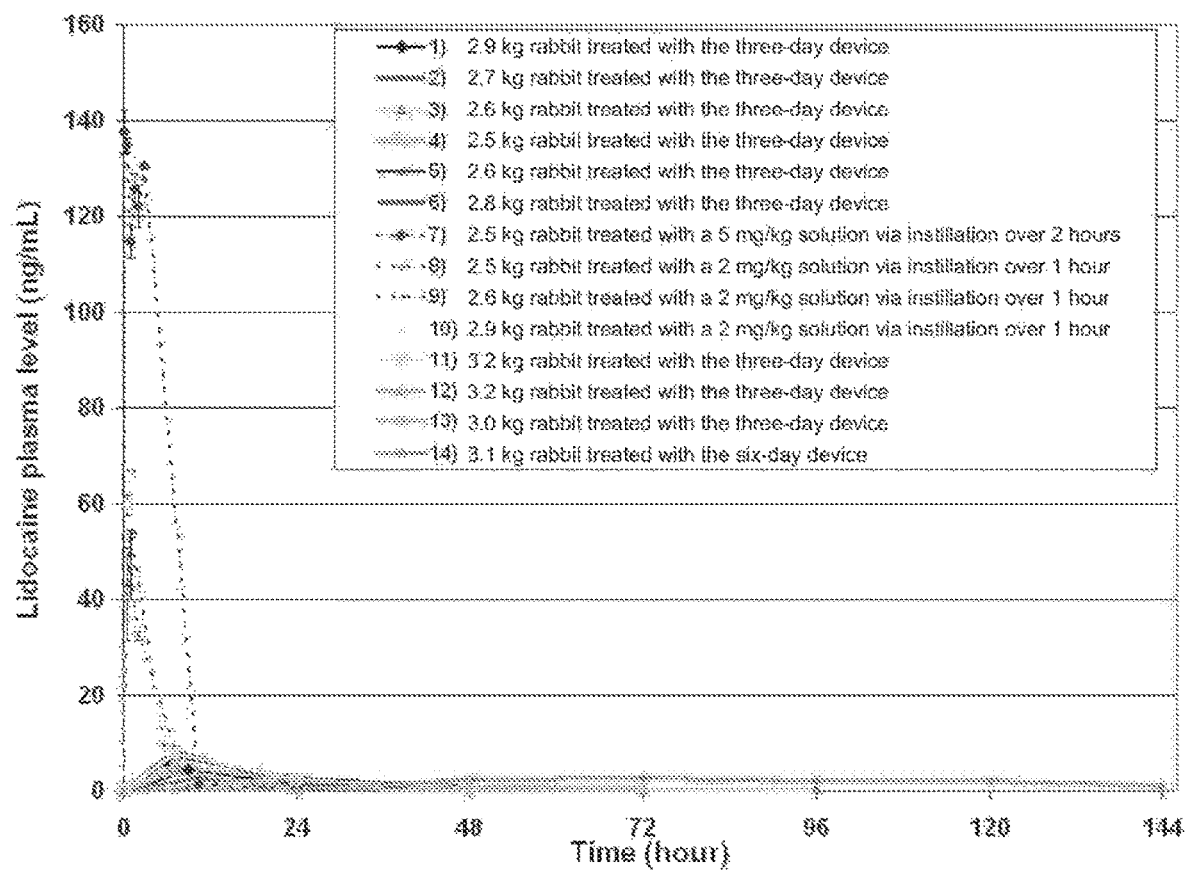
FIG. 22 is a graph illustrating lidocaine plasma concentration over time exhibited for various instillations and implanted devices in vivo in rabbit bladder.
Figure 23:
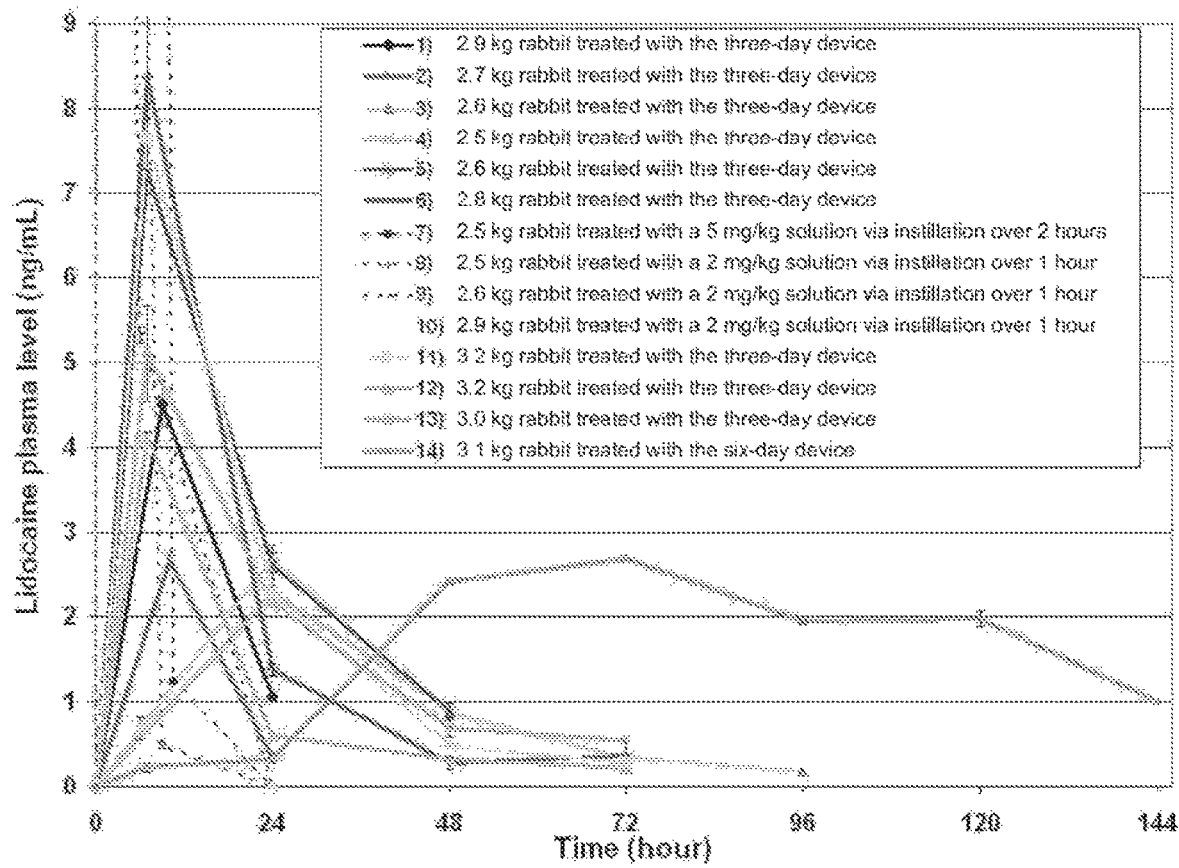
FIG. 23 a graph illustrating lidocaine plasma concentration over time, exhibited for various instillations and implanted devices in vivo in rabbit bladder, with the y-axis modified.

The blood, bladder and urine samples were analyzed to determine the lidocaine concentration in plasma, bladder tissue, and urine. FIG. 22 is a graph illustrating lidocaine plasma concentration over time for the various treatments, and FIG. 23 is the same graph with the y-axis modified. In these graphs, instillation treatments are shown with dotted lines and the device treatments are shown with solid lines. The key indicates the weight of each rabbit along with the treatment type. The data presentation in FIG. 22 generally permits comparing the various instillation treatments to the various intravesical implant treatments, while the data presentation in FIG. 23 generally permits comparing the various intravesical implant treatments to each other.

As shown in FIG. 22, instillation of the lidocaine solution resulted in an initial surge of lidocaine plasma concentration, but lidocaine was no longer detected in the plasma after one day. Thus, instillation treatment permits a sudden increase in lidocaine plasma concentration, but this increase is quickly followed by a rapid decline. In the case of the rabbit treated via instillation of a 5 mg/kg lidocaine solution for two hours, the peak plasma concentration exceeded 100 ng/mL, which is within the known toxicity limit of lidocaine by a factor of ten. However, such high initial peak concentrations may be necessary to provide relief between repeated instillations, even though systemically undesirable.

FIG. 22 also shows that lidocaine plasma concentration was relatively lower in rabbits treated with the implanted device than in rabbits treated via instillation. However, the rabbits treated with the implanted device maintained a relatively higher lidocaine plasma concentration with the passage of time.

FIG. 23 shows that release from the three-day device slowed after twelve hours, which is consistent with the results obtained in the in vitro release study of Example 6. The six-day device, which had twice the payload of the three-day device, demonstrated a more extended release profile. However, the six-day device demonstrated an initial induction time, which is consistent with the results obtained in the in vitro release study of Example 6. The induction time is attributable to the thicker tube used for the six-day device, which is hydrated over the induction time to initiate lidocaine release from the device. All in all, the results show that the delivery of a depot of lidocaine via an implanted device, when compared to delivery via instillation, may permit maintaining relatively higher lidocaine plasma concentrations with the passage of time while avoiding high peak lidocaine plasma concentrations.

Figure 24:
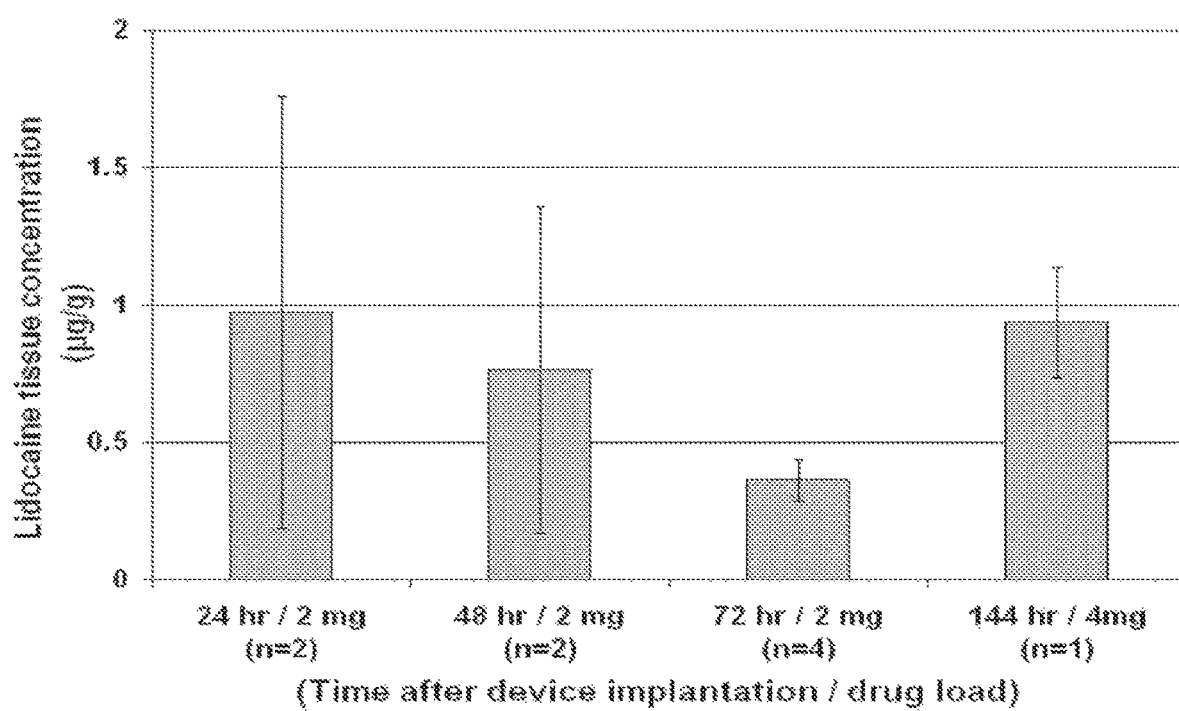
FIG. 24 is a graph illustrating the lidocaine tissue concentration over time, exhibited for various implanted devices in vivo in rabbit bladder.

Because the target site for intravesical treatment is bladder tissue, the bladder tissue concentration of lidocaine is a more direct index of the efficacy of treatment via an intravesical implant than the plasma concentration. FIG. 24 shows lidocaine concentration in bladder tissue over time for various treatments via intravesical implant. Lidocaine tissue concentrations are shown for a three-day device at multiple time points after implantation, including one day after implantation, two days after implantation, and three days after implantation. In other words, the device was not necessarily retained in the bladder for three days. Lidocaine tissue concentrations are also shown for a six-day device at the time point of six days after implantation. As shown, the three-day device exhibited decreasing lidocaine tissue concentration over the course of three days, while the six day device exhibited lidocaine tissue concentrations after six days that compared to the lidocaine tissue concentrations exhibited by the three-day device after one day. Lidocaine tissue concentrations were also measured one day after intravesical instillation, but the tissue concentration was below the level of detection. It also should be noted that the lidocaine tissue concentration is on the order of micrograms per gram of tissue.

Figure 25:
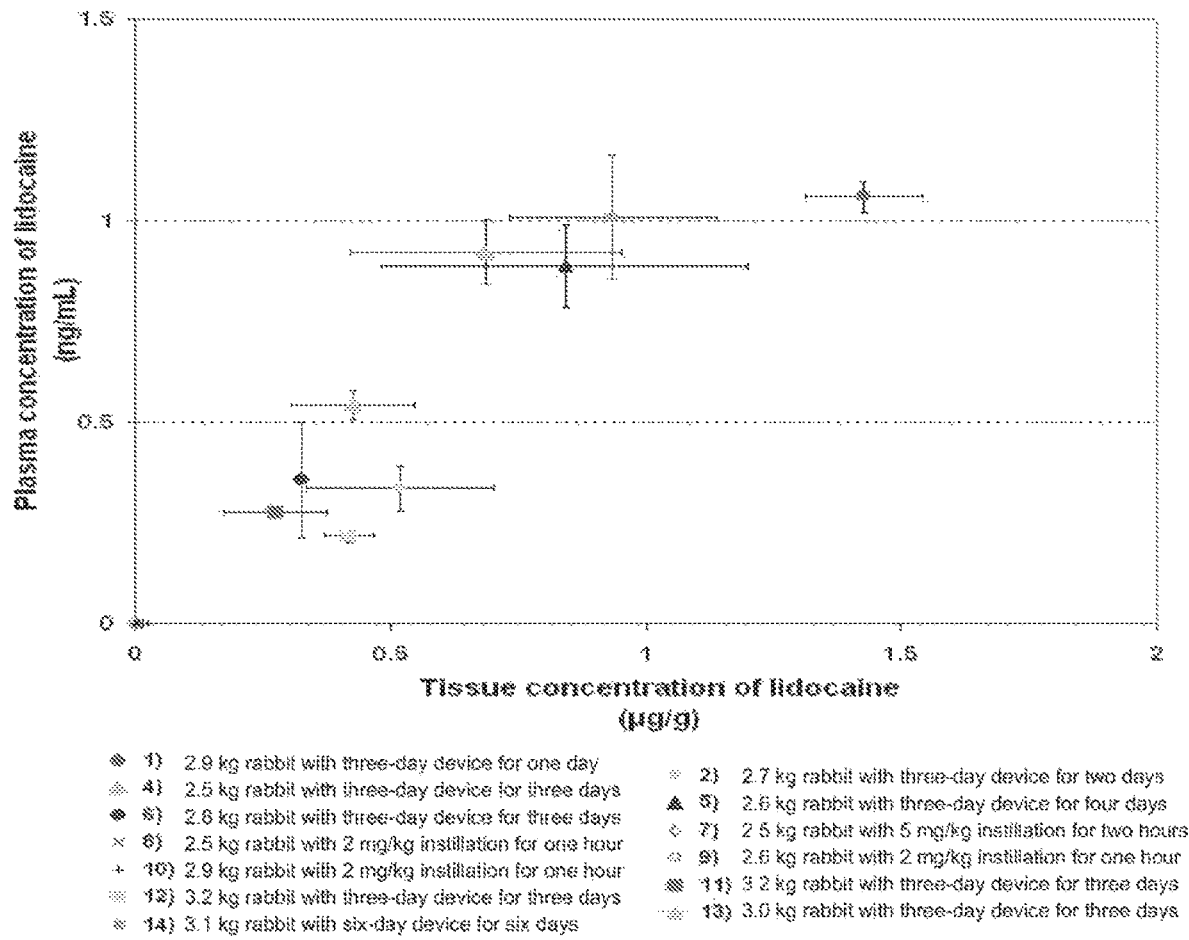
FIG. 25 is a graph illustrating the correlation between lidocaine tissue concentration and lidocaine plasma concentration, exhibited for various instillations and implanted devices in vivo in rabbit bladder.

FIG. 25 shows the correlation between lidocaine plasma concentration and lidocaine tissue concentration for the intravesical implants. Correlations are also shown for the instillation treatments one day after instillation, but these concentrations are negligible in comparison with the device treatments. As shown, higher lidocaine plasma concentrations are generally associated with higher lidocaine tissue concentrations. However, the lidocaine tissue concentrations are approximately one thousand times higher than the lidocaine plasma concentration. Therefore, delivery of a depot of lidocaine via an implanted device may provide higher drug exposure to the bladder tissue while avoiding the high peak plasma concentration.

Figure 26:
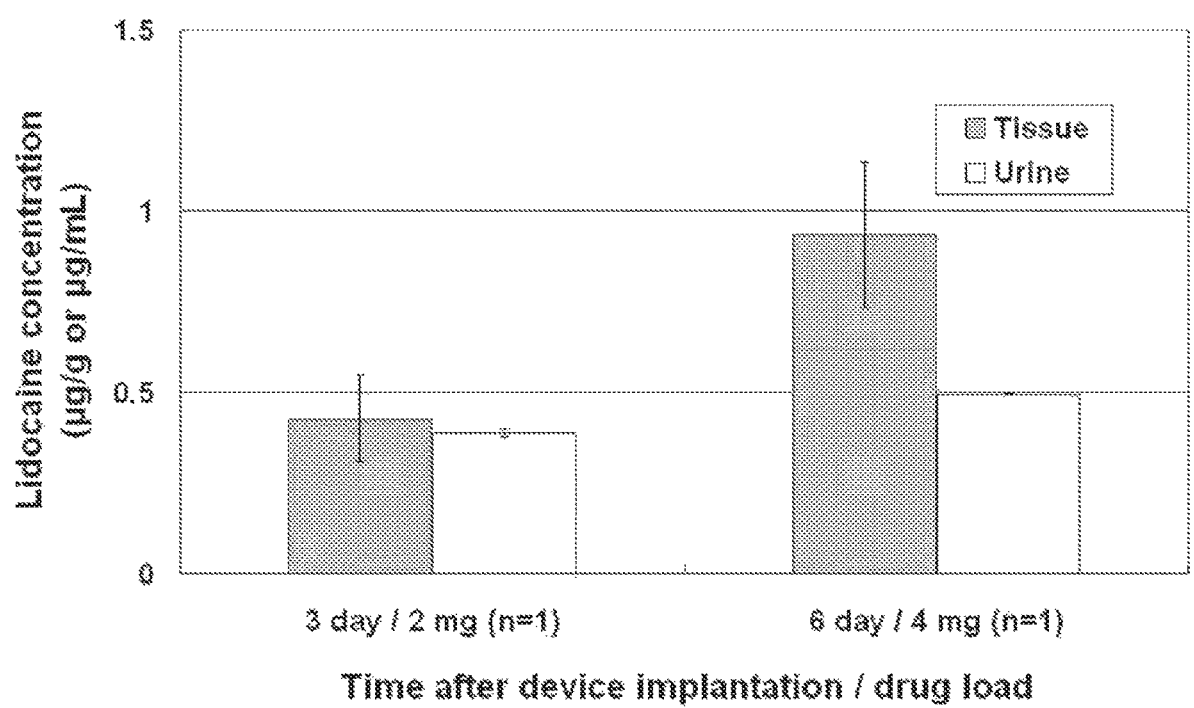
FIG. 26 is a graph illustrating lidocaine concentration in tissue and urine, exhibited by devices implanted in vivo in rabbit bladder for three days and for six days.

Lidocaine urine concentration was also measured for two animals that were treated with the three-day device and six-day device, respectively. The results are shown in FIG. 26. Bladder tissue and urine samples were collected three days after implantation for the rabbit that received the three-day device and six days after implantation for the rabbit that received the six-day device. As shown, the order of magnitude of the lidocaine urine concentration was comparable to the lidocaine tissue concentration, which comports with in vitro studies described below with reference to Example 9 and FIG. 27, below.

EXAMPLE 9

In Vitro Absorption of Lidocaine in Rat Bladder

A study was performed on rat bladders in vitro to investigate the effect of pH and time on lidocaine absorption into the urothelium of the bladder. A number of different lidocaine solutions were made from artificial urine and radio-labeled lidocaine. Each lidocaine solution had a lidocaine concentration of either $10^{-5}\%$ ($10^{-4}$ mg/mL) or 1% (10 mg/mL), and a pH ranging from 4.0 to 8.5.

Rat bladders were inverted to expose the urothelium or inner lining of the bladder. The inverted bladders were placed in the lidocaine solutions, each lidocaine solutions having a different concentration and pH. The bladders were incubated in the lidocaine solutions for one of the following amounts of time: ten minutes, one hour, one day, three days or five days. After the designated incubation time expired, each bladder was removed from the lidocaine solution and the lidocaine concentration in the in the tissue was determined.

Figure 27:
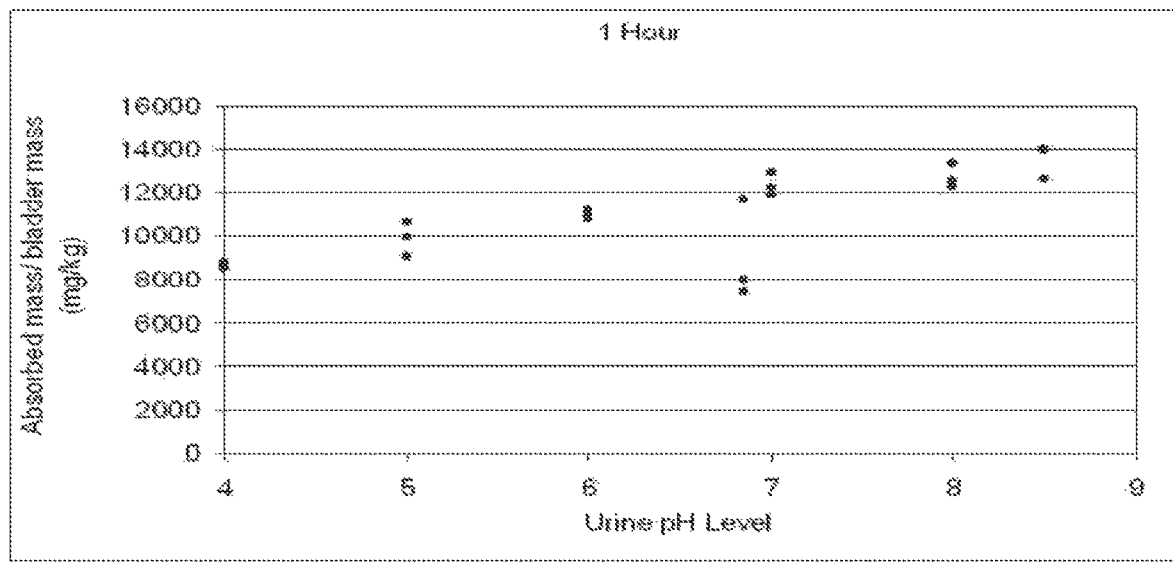
FIG. 27 is a graph illustrating the effect of pH on the absorption of lidocaine, exhibited during studies performed in vitro on rat bladder for one hour and for one day, respectively.
Figure 27:
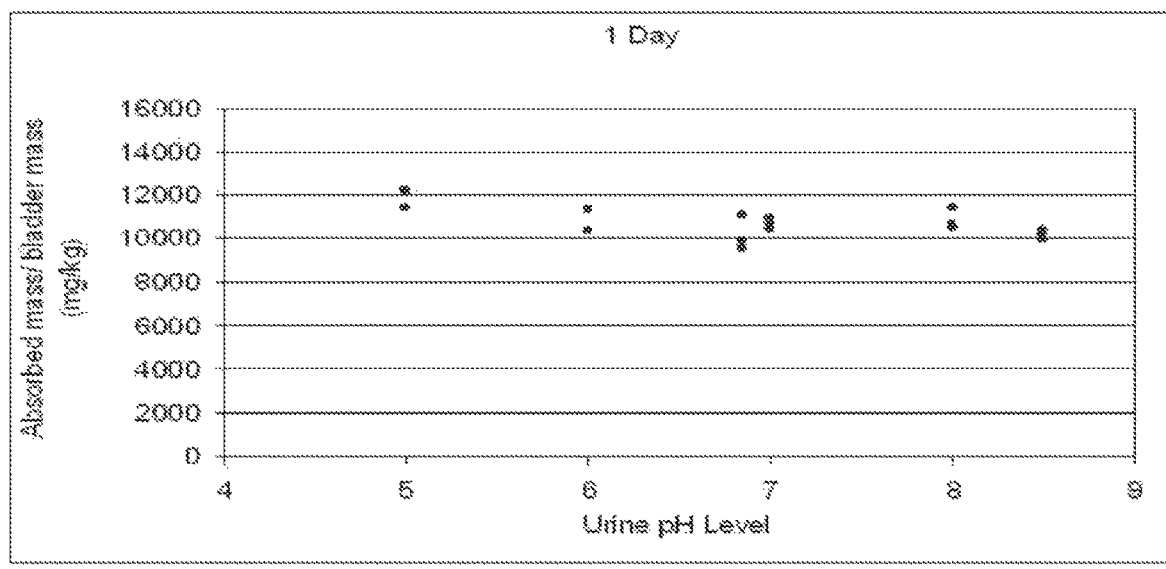

FIG. 27 is a graph illustrating the effect of pH on the absorption of lidocaine solution in vitro into the tissue of rat bladder, for time periods of one hour and for one day. The graph pertains to the lidocaine solution having a 1% lidocaine concentration only. As shown, the pH of the lidocaine solution slightly affected the absorption of lidocaine into the bladder tissue after one hour, but the pH did not significantly affect lidocaine absorption after one day. For each bladder, the plateau tissue concentration (or absorbed lidocaine mass per bladder tissue mass) was about 10000 mg/kg or 1%, which was the lidocaine concentration of the lidocaine solution in which the bladder was immersed. This result implies that the topical absorption of lidocaine into the bladder over an extended time period can be independent of the pH of the lidocaine solution. This result also indicates that buffering the lidocaine solution may not be necessary for topical absorption of lidocaine by the urothelium via long term in vivo exposure in the bladder.

Figure 28:
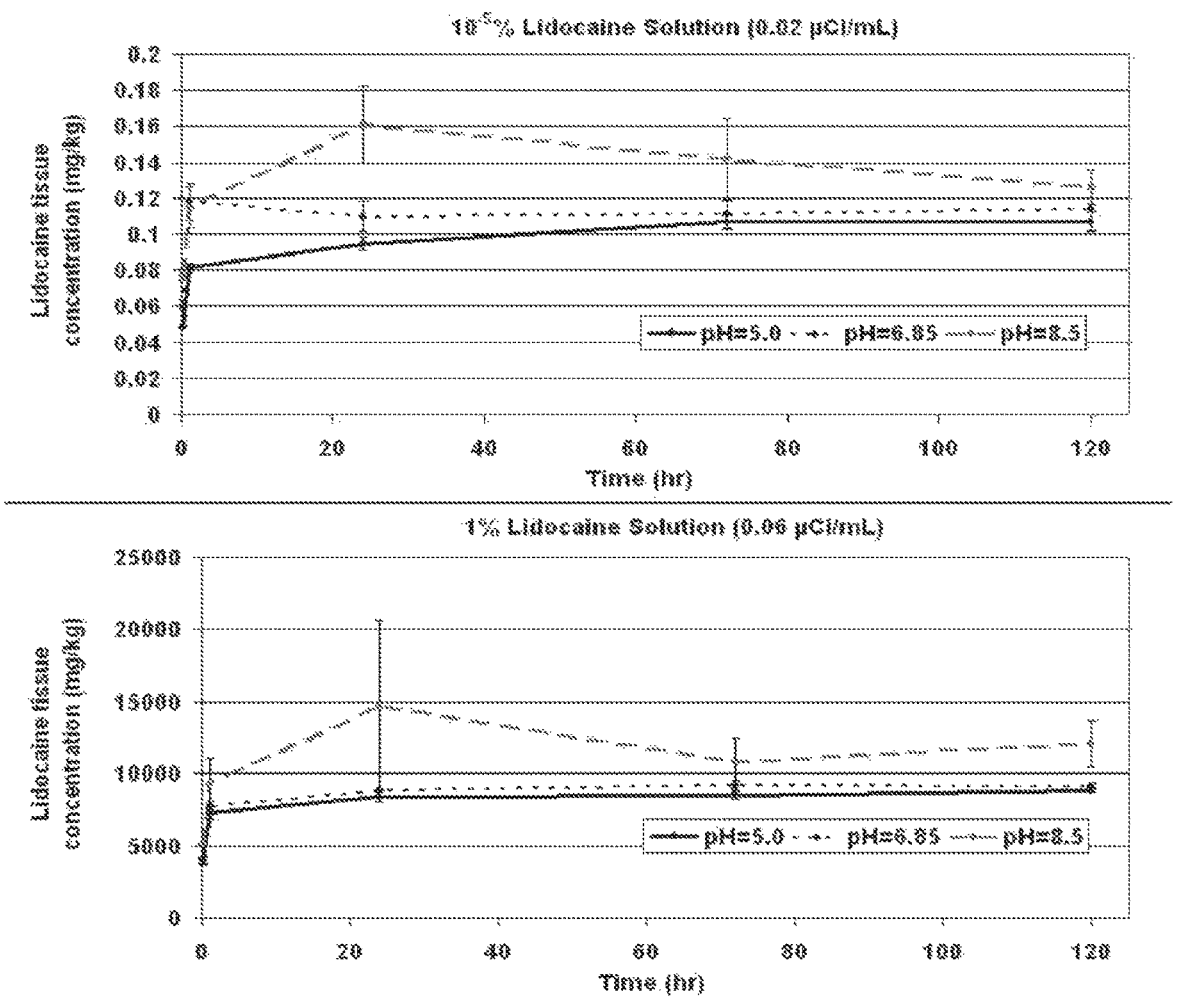
FIG. 28 is a graph illustrating lidocaine tissue concentration over time, exhibited during studies performed in vitro on rat bladder with $10^{-5}$% and 1% lidocaine solutions of varying pH.

FIG. 28 is a graph illustrating lidocaine tissue concentration over time, exhibited during studies performed in vitro on rat bladder with $10^{-5}\%$ and 1% lidocaine solutions of varying pH. The graph shows the effect of lidocaine concentration and pH on the absorption of lidocaine into rat bladder tissue over time. Results for lidocaine solutions having $10^{-5}\%$ concentration are plotted separately from those having 1% concentration. As shown, lidocaine tissue concentration increases quickly (within about ten minutes) and reach a plateau for both $10^{-5}\%$ and 1% lidocaine solutions. As shown, the plateau lidocaine tissue concentration for the $10^{-5}\%$ lidocaine solution is in the order of 0.1 mg/kg or $10^{-5}\%$, while he plateau lidocaine tissue concentration for the 1% lidocaine solution is in the order of 10000 mg/kg or 1%. This result shows that the partition coefficient for lidocaine tissue to lidocaine solution is about unity for in vitro lidocaine absorption into urothelium. Higher lidocaine concentration shows higher lidocaine absorption into urothelium.

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

We claim:

1. A method for administration of a drug into a patient's bladder, comprising:
    inserting a distal end of a lumen device through a patient's urethra and into the patient's bladder, wherein an opposing proximal end of the lumen device remains outside of the patient;
    driving an elastically deformed drug delivery device out of a lumen in the distal end of the lumen device and into the bladder and out of the lumen, whereupon exiting the lumen, the drug delivery device immediately returns to an undeformed coiled shape for retention in the bladder;
    removing the lumen device from the patient's urethra; and
    releasing a drug from the drug delivery device into the patient's bladder,
    wherein the drug delivery device comprises an elastic wire retention frame which in the undeformed coiled shape has exactly two smaller arches sharing a single common larger arch, wherein the three arches resist compression and prevent collapse of the drug delivery device and thereby impede voiding of the drug delivery device from the bladder.

2. The method of claim 1, wherein the lumen device comprises a urethral catheter.

3. The method of claim 1, wherein the lumen device comprises a cystoscope.

4. The method of claim 1, wherein the elastic wire retention frame comprises a superelastic alloy.

5. The method of claim 1, wherein the elastic wire retention frame comprises a spring constant from 3 N/m to 60 N/m.

6. The method of claim 1, wherein the elastic wire retention frame comprises a spring constant from 3.6 N/m to 3.8 N/m.

7. The method of claim 1, wherein the drug is released through an aperture in the drug delivery device, driven by osmotic pressure.

8. The method of claim 1, wherein the drug delivery device has no aperture and the drug is released by diffusion through a wall in the drug delivery device.

9. The method of claim 1, wherein a stylet is used to push the drug delivery device out of the lumen in the distal end of the lumen device.

10. The method of claim 1, wherein the drug is released from the drug delivery device continuously over a period from 7 days to 90 days.

11. The method of claim 1, wherein the drug delivery device is non-resorbable.

12. The method of claim 1, wherein the drug delivery device further comprises a drug reservoir portion aligned with the elastic wire retention frame.

13. The method of claim 12, wherein the drug reservoir portion comprises an elongated tube, an interior of which defines a reservoir in which a drug formulation is housed.

14. The method of claim 13, wherein the elongated tube comprises an aperture for releasing the drug therethrough by osmotic pressure.

15. A method for administration of a drug into a patient's bladder, comprising:
inserting a distal end of a lumen device through a patient's urethra and into the patient's bladder, wherein an opposing proximal end of the lumen device remains outside of the patient;
driving an elastically deformed drug delivery device out of a lumen in the distal end of the lumen device and into the bladder and out of the lumen, whereupon exiting the lumen, the drug delivery device immediately returns to an undeformed coiled shape for retention in the bladder, wherein the drug delivery device comprises a non-resorbable elastomeric tube, which has a central channel, and a drug formulation disposed within the central channel, the drug formulation comprising the drug;
removing the lumen device from the patient's urethra; and
releasing the drug from the drug delivery device into the patient's bladder,
wherein the drug delivery device comprises an elastic wire retention frame which in the undeformed coiled shape has exactly two smaller arches sharing a single common larger arch, wherein the three arches resist compression and prevent collapse of the drug delivery device and thereby impede voiding of the drug delivery device from the bladder.

16. The method of claim 15, wherein the drug formulation is in solid form.

17. The method of claim 16, wherein, after exiting the lumen device, urine in the bladder permeates through the elastomeric tube, contacts the drug formulation, and solubilizes the drug before said releasing of the drug.

18. The method of claim 15, wherein the elastic wire retention frame comprises a spring constant from 3.6 N/m to 3.8 N/m.

19. The method of claim 15, wherein the elastic wire retention frame has a Young's modulus from about 25 MPa to about 30 MPa.

20. The method of claim 15, wherein the elastic wire retention frame comprises a spring constant from 3 N/m to 60 N/m.

21. A method for administration of a drug into a patient's bladder, comprising:
providing a lumen device, which has a distal end, an opposing proximal end, and an open lumen extending therebetween;
inserting the distal end of the lumen device into the bladder of a patient in need of treatment, where the proximal end of the lumen device remains outside of the patient;
deforming an implantable medical device for controlled drug delivery and passing it into the proximal end of the lumen of the lumen device, wherein the implantable medical device comprises (i) at least one drug reservoir component comprising a drug;
and (ii) a vesicle retention frame which comprises an elastic wire having a first end, an opposing second end, and an intermediate region therebetween, wherein the drug reservoir component is attached to the intermediate region of the vesicle retention frame;
driving the deformed device through the lumen and out of the lumen, whereupon the implantable medical device returns to its undeformed shape for retention in the bladder;
removing the lumen device from the patient; and
releasing the drug from the implantable medical device,
wherein the undeformed shape for retention in the bladder has exactly two smaller arches sharing a single common larger arch.

22. The method of claim 21, wherein the lumen device comprises a catheter and a stylet is used in driving the deformed device through the lumen and out of the lumen, and wherein the implantable medical device changes shape as it emerges from the catheter.

23. The method of claim 21, wherein the patient is in need of treatment for interstitial cystitis, overactive bladder syndrome, or bladder cancer.

24. The method of claim 21, wherein the elastic wire comprises a spring constant from 3 N/m to 60 N/m.

25. The method of claim 21, wherein the elastic wire comprises a spring constant from 3.6 N/m to 3.8 N/m.

26. The method of claim 21, wherein the elastic wire has a Young's modulus from about 25 MPa to about 30 MPa.

* * * * *